United States Patent [19]

Naito et al.

[11] 4,198,506

[45] Apr. 15, 1980

[54] 2-CARBOXYALKYL-2,3-DIHYDRO-6-MERCAPTO-S-TRIAZOLO[4,3-b]-PYRIDAZIN-3-ONES

[75] Inventors: Takayuki Naito, Kawasaki; Jun Okumura, Yokohama; Hajime Kamachi, Ichikawa; Seiji Iimura, Tokyo; Hideaki Hoshi, Ichikawa; Masahisa Oka, Yokohama, all of Japan

[73] Assignee: Bristol-Myers Company, New York, N.Y.

[21] Appl. No.: 22,408

[22] Filed: Mar. 21, 1979

Related U.S. Application Data

[60] Division of Ser. No. 877,132, Feb. 13, 1978, Pat. No. 4,151,352, which is a division of Ser. No. 784,885, Apr. 5, 1977, Pat. No. 4,082,912, which is a continuation-in-part of Ser. No. 701,443, Jun. 30, 1976, abandoned.

[51] Int. Cl.² .......................................... C07D 487/04
[52] U.S. Cl. ................................................... 544/236
[58] Field of Search .................................. 544/236, 26

[56] References Cited

U.S. PATENT DOCUMENTS

| 3,907,786 | 9/1975 | Naito et al. | 544/26 |
| 3,994,898 | 11/1976 | Hoehn et al. | 544/236 |

*Primary Examiner*—Paul M. Coughlan, Jr.
*Attorney, Agent, or Firm*—H. W. Taylor, Jr.

[57] ABSTRACT

Certain 7-acylamido-3-(2-carboxyalkyl-2,3-dihydro-s-triazolo[4,3-b]pyridazin-3-on-6-ylthiomethyl)-3-cephem-4-carboxylic acids and their salts and easily hydrolyzed esters of the 4-carboxyl group were synthesized and found to be potent antibacterial agents which exhibited good aqueous solubility. A preferred embodiment was 7-[o-(methylaminomethyl)phenylacetamido]-3-(2-carboxyalkyl-2,3-dihydro-s-triazolo[4,3-b]pyridazin-3-on-6-ylthiomethyl)-3-cephem-4-carboxylic acid.

3 Claims, No Drawings

2-CARBOXYALKYL-2,3-DIHYDRO-6-MERCAPTO-S-TRIAZOLO[4,3-b]-PYRIDAZIN-3-ONES

CROSS REFERENCE TO RELATED APPLICATIONS

This application is a division of our prior, copending application Ser. No. 877,132 filed Feb. 13, 1978, U.S. Pat. No. 4,151,352, which in turn was a division of application Ser. No. 784,885 filed Apr. 5, 1977 and issued Apr. 4, 1978 as U.S. Pat. No. 4,082,912, which in turn was a continuation-in-part of our prior, copending application Ser. No. 701,443 filed June 30, 1976 and now abandoned.

BACKGROUND OF THE INVENTION

1. Field of the Invention

The cephalosporins of the present invention in general possess the usual attributes of such compounds and are particularly useful in the treatment of bacterial infections.

2. Description of the Prior Art

The cephalosporins are a well-known group of semi-synthetic antibacterial agents made originally, for example, by acylation of the 7-amino group of the nucleus 7-aminocephalosporanic acid (7-ACA) and later by similar acylation of nuclei derived therefrom, as by modification of its substituent at the 3-position. Various reviews have appeared in the scientific literature (e.g. Cephalosporins and Penicillins - Chemistry and Biology, edited by Edwin H. Flynn, Academic Press, New York, 1972, and particularly pages 554–569) and in the patent literature, e.g. as in U.S. Pat. Nos. 3,687,948; 3,741,965; 3,743,644; 3,759,904; 3,759,905; 3,766,175; 3,766,906; 3,769,281; 3,796,801; 3,799,923; 3,812,116; 3,813,388; 3,814,754 and 3,814,755 (all U.S. Class 260-243C).

Issued patents on 3-thiolated cephalosporins in which the 7-substituent is (a) α-Amino-α-phenylacetamido include U.S. Pat. Nos. 3,641,021; 3,734,907; 3,687,948; 3,741,965; 3,757,015; 3,743,644, Japan No. 71/24400 (Farmdoc 46374S), Belgium No. 776,222 (Farmdoc 38983T; U.K. No. 1,328,340 which includes various substituents on the benzene ring), Belgium No. 772,592 (Farmdoc 19696T; U.S. Pat. Nos. 3,687,948, 3,734,907 and 3,757,012), West Germany No. 2,202,274 (Farmdoc 50428T) corresponding to U.S. Pat. No. 3,759,904, Netherlands No. 7205644 (Farmdoc 76309T; U.S. Pat. No. 3,757,014); and (b) o-, m- or p-aminoethoxyphenylacetamido as Netherlands No. 72/13968 (Farmdoc 2474OU) corresponding to U.S. Pat. No. 3,759,905 and (c) o-aminomethylphenylacetamido as U.S. Pat. Nos. 3,766,176 and 3,766,175 (which also review the older patent literature concerning substituted 7-phenylacetamidocephalosporanic acids) and (d) N-(phenylacetimidoyl)aminoacetamido as U.S. Pat. No. 3,692,779; and (e) α-amino-α-(1,4-cyclohexadienyl)acetamido as in Belgium No. 776,222 (Farmdoc 38983T; U.K. No. 1,328,340).

Additional similar disclosures are found in U.S. Pat. No. 3,692,779 (Belgium No. 771,189; Farmdoc 12819T), Japan No. 72/05550 (Farmdoc 12921T), Japan No. 72/05551 (Farmdoc 12922T), U.S. Pat. No. 3,719,673 (Belgium No. 759,570; Farmdoc 39819S), Belgium No. 793,311 (Farmdoc 39702U) and Belgium No. 793,191 (Farmdoc 39684U).

Issued disclosures of 3-thiolated cephalosporins in which the 7-substituent is 7-mandelamido (7-α-hydroxyphenylacetamido) are found, for example, in U.S. Pat. No. 3,641,021, France No. 73.10112, U.S. Pat. No. 3,796,801, Great Britain No. 1,328,340 (Farmdoc 38983T), U.S. Pat. No. 3,701,775, Japan No. 48-44293 (Farmdoc 55334U) and in Hoover et al., J. Med. Chem. 17(1), 34–41 (1974) and Wick et al., Antimicrobial Ag. Chemo., 1(3), 221–234 (1972).

U.S. Pat. No. 3,819,623 (and, for example, also U.K. No. 1,295,841 and West Germany No. 1,953,861) discloses specifically and with working details the preparation of 2-mercapto-1,3,4-thiadiazole-5-acetic acid and its conversion to 7-(1H-tetrazol-1-yl-acetamido)-3-(5-carboxymethyl-1,3,4-thiadiazol-2-ylthiomethyl)-3-cephem-4-carboxylic acid which is also disclosed in West Germany Offenlegungsschrift No. 2,262,262.

U.S. Pat. Nos. 3,766,175 and 3,898,217 disclose a compound of the formula

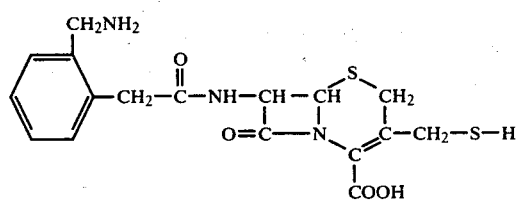

wherein R is

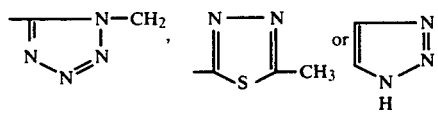

or a nontoxic, pharmaceutically acceptable salt thereof, and

A compound of the formula

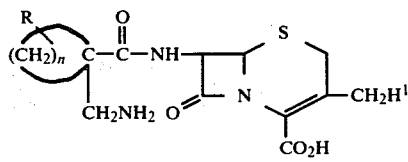

wherein
R is —H or lower alkyl;
R¹ is —H, (lower)alkanoyloxy,

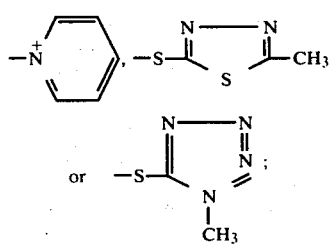

n is an integer from 4–7, inclusive; and the pharmaceutically acceptable addition salts thereof, respectively.

U.S. Pat. Nos. 3,883,520 and 3,931,160 and Farmdoc Abstract 22850W make reference to 3-heterocyclicthiomethyl cephalosporins containing a number of substituents (including carboxyl) on the numerous heterocycles included but these references are completely general in nature and include no physical constants, yields, methods of synthesis or the like and do not even name any such compound containing a carboxyl substituent.

U.S. Pat. No. 3,928,336 provides a review of much of the older cephalosporin art.

U.S. Pat. Nos. 3,907,786 and 3,946,000 disclose cephalosporins containing various fused ring bicyclic thiols.

Farmdoc abstract 18330X discloses compounds of the formula

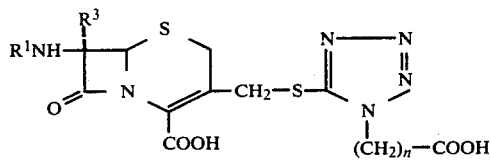

(where $R^1$=acyl or H; $R^3$=H or methoxy; n=1-9).

SUMMARY OF THE INVENTION

The present invention provides compounds having the structure:

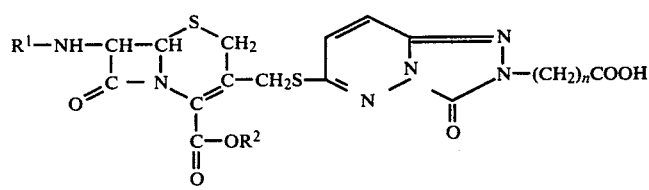

(often written herein as

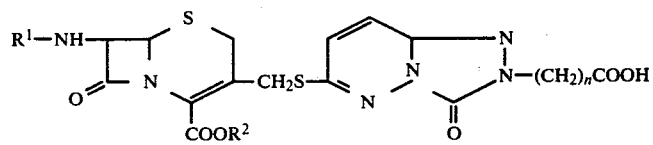

wherein n is one or two and $R^1$ is acyl or hydrogen and $R^2$ is hydrogen or the group having the formula

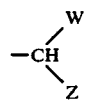

wherein, when W represents hydrogen, Z represents (lower)alkanoyl, benzoyl, naphthoyl, furoyl, thenoyl, nitrobenzoyl, methylbenzoyl, halobenzoyl, phenylbenzoyl, N-phthalimido, N-succinimido, N-saccharino, N-(lower)alkylcarbamoyl, (lower)alkoxy, (lower)-alkylthio, phenoxy, carbalkoxy, carbobenzoxy, carbamoyl, benzyloxy, chlorobenzyloxy, carbophenoxy, carbo-tert.-butoxy or (lower)alkylsulfonyl, and when W represents carbalkoxy, Z represents carbalkoxy and, when W represents phenyl, Z represents benzoyl or cyano or wherein W and Z taken together represent 2-oxocycloalkyl containing 4 to 8 carbon atoms inclusive. In the preferred embodiments of this invention $R^2$ is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl.

As set forth below in more detail the present invention also provides salts of these acids. The stereochemistry of the bicyclic nucleus is that found in Cephalosporin C.

Acyl ($R^1$) comprises the groups having the structures:

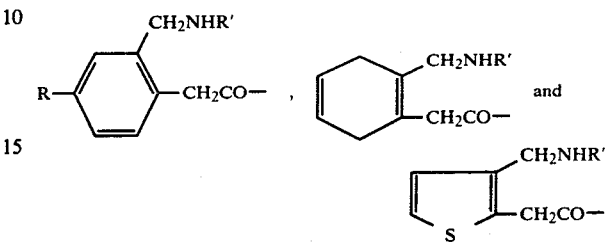

wherein R is hydrogen, hydroxy or methoxy and R' is hydrogen or methyl.

A preferred embodiment of the present invention consists of the compounds of Formula I wherein $R^1$ has the structure

I

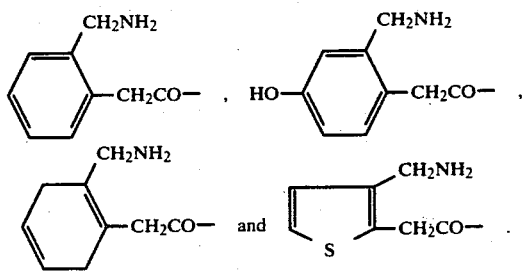

Another preferred embodiment of the present invention consists of the compounds of Formula I wherein $R^1$ has the structure

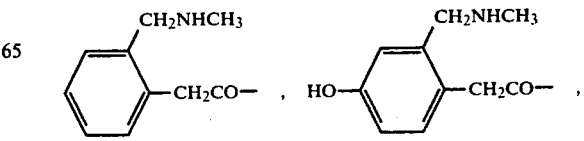

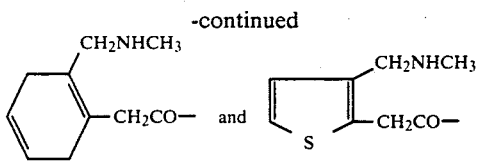

The present invention also provides the process for the production of the antibacterial agents having the structure

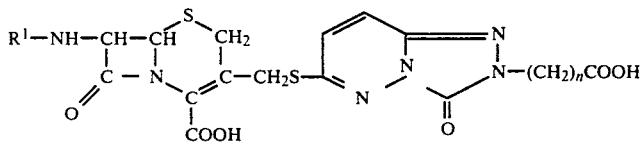

wherein n is one or two and $R^1$ is acyl as defined above which comprises reacting a compound of the formula

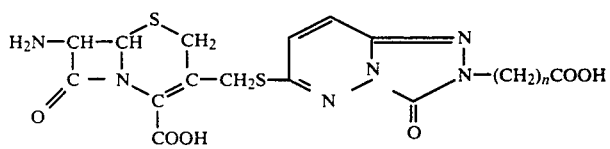

wherein n is one or two or a salt or easily hydrolyzed ester or Schiff base as with benzaldehyde or salicylaldehyde thereof (including, but not limited to, those of U.S. Pat. No. 3,284,451 and U.K. No. 1,229,453 and any of the silyl esters described in U.S. Pat. No. 3,249,622 for use with 6-aminopenicillanic acid and used in Great Britain No. 1,073,530 and particularly the pivaloyloxymethyl, acetoxymethyl, methoxymethyl, acetonyl, phenacyl, p-nitrobenzyl, $\beta,\beta,\beta$-trichloroethyl, 3-phthalidyl and 5-indanyl esters) thereof with an organic monocarboxylic acid chloride or a functional equivalent thereof as an acylating agent.

Such functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester or thioester (e.g. with p-nitrophenyl, 2,4-dinitrophenol, thiophenol, thioacetic acid) may be used or the free acid itself may be coupled with compound II after first reacting said free acid with N,N'-dimethylchloroformiminium chloride [cf. Great Britain 1,008,170 and Novak and Weichet, Experientia XXI, 6, 360 (1965)] or by the use of enzymes or of an N,N'-carbonyldiimidazole or an N,N'-carbonylditriazole [cf. South African patent specification 63/2684] or a carbodiimide reagent [especially N,N'-dicyclohexylcarbodiimide. N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkylylamine reagent [cf. R. Buijle and H. G. Viehe, Angew. Chem. International Edition 3, 582, (1964)] or of an isoxazolium salt reagent [cf. R. B. Woodward, R. A. Olofson and H. Mayer, J. Amer. Chem. Soc., 83, 1010 (1961)], or of a ketenimine reagent [cf. C. L. Stevens and M. F. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. 3,682,777.

For the coupling of the organic carboxylic acid as described above which compound II (or a salt or preferably an easily hydrolyzed ester of Schiff base, as with benzaldehyde, thereof) it is also convenient and efficient to utilize as the coupling agent phosphonitrilic chloride trimer (J. Org. Chem., 33(7), 2979–81, 1968) or N-ethoxy-1,2-dihydroquinoline (EEDQ) as described in J. Amer. Chem. Soc., 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a 7-acylaminocephalosporanic acid (prepared by substituting 7-aminocephalosporanic acid for the 3-thiolated-7-aminocephalosporanic acids in the acylation procedures described herein and elsewhere reported) with a thiol HSR³ having the formula

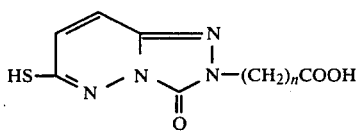

wherein n is one or two and then removing the protecting group if any is present, as on the aminomethyl or methylaminomethyl group or on the carboxyl group or both. The displacement of such a 3-acetoxy group with such a thiol may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. As noted above, the preparation of many other 7-acylamidocephalosporanic acids is described in the patent and scientific literature, e.g. in U.S. Class 260-243C.

When the organic carboxylic acid contains a functional group such as amino or methylamino it is often desirable to first block (or protect) said group, then carry out the coupling reaction and finally subject the resulting compound to chemical removal of the protecting group, that is, subjecting the resulting compound to elimination reaction of the protecting group.

The salts of the compounds of this invention include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)-alkylpiperidine, e.g. N-ethylpiperidine, and other amines which have been used to form salts with benzylpenicillin; and the nontoxic acid addition salts thereof (i.e., the amine salts) including the mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate and the like.

Also included in this invention are the compounds (used as either intermediates or metabolic precursors) in which the amino group is "blocked" by substituents such as 2-iodoethoxycarbonyl (U.K. No. 1,349,673), t-butoxycarbonyl, carbobenzyloxy, formyl, o-nitrophenylsulfenyl, β,β,β-trichloroethoxycarbonyl, 4-oxo-2-pentenyl-2, 1-carbomethoxy-1-propenyl-2- and the like. Particularly included in such blocking groups are the ketones (especially acetone) and aldehydes (especially formaldehyde and acetaldehyde) disclosed, for example, in U.S. Pat. Nos. 3,198,804 and 3,347,851 and the β-ketoesters and β-diketones disclosed, for example, in U.S. Pat. No. 3,325,479 and the β-ketoamides disclosed in Japan No. 71/24714 (Farmdoc 47,321S).

The preferred esters of the cephalosporins of the present invention are the pivaloyloxymethyl, acetoxymethyl, methoxymethyl, acetonyl and phenacyl esters.

All are useful intermediates in the production of the cephalosporin having a free carboxyl group.

As indicated above, these five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767-773 (1971). In another good method the triethylamine salt of 7-aminocephalosporanic acid is reacted directly with the active halogen compound, as in United Kingdom No. 1,229,453.

These esters of 7-aminocephalosporanic acid are then reacted with the nucleophile HSR³ in the same manner as is illustrated herein for 7-aminocephalosporanic acid itself. The 3-thiolated ester of 7-aminocephalosporanic acid is then coupled with the organic carboxylic acid R'-OH as before. Before or after removal of any blocking group, e.g. on an amino group in the 7-sidechain, the ester of the cephalosporin so obtained is, if not used per se, converted to its free acid, including its zwitterion (and, if desired, any salt) by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006-2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

In the treatment of bacterial infections in man, the compounds of this invention are administered parenterally in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excepients. The dosage units are in the form of liquid preparations such as solutions or suspensions.

The other reagents used to prepare the compounds of the present invention are synthesized either as described in the art (e.g. as in the patents and publications noted above) or by strictly analogous procedures. For convenience and purposes of illustration, however, there are given below some specific examples of such syntheses, e.g. to prepare carboxylic acids containing a free amino group which is "blocked" with tert.-butoxycarbonyl.

2-(tert.-Butoxycarbonylaminomethyl)-1,4-cyclohexadienylacetic acid

A solution of 16.5 g. (0.1 mole) of o-aminomethylphenylacetic acid in 1.5 l of liquid ammonia (which had been treated with 50 mg. of Li to remove a trace of moisture) was slowly diluted with 500 ml. of dry t-BuOH. To the solution was added in small portions 3.4 g. (0.5 atom) of Li over a period of 4 hours and the mixture was stirred for 16 hours at room temperature removing the liquid ammonia in a hood and finally evaporated to dryness below 40° C. The residue was dissolved in 500 ml. of water and the solution was chromatographed on a column of IR-120 (H+, 700 ml.) resin and eluted with 1% NH4OH solution. Ninhydrin positive fractions of the eluate were combined and evaporated to dryness. The residue was washed with four 50 ml. portions of hot acetone and recrystallized from 500 ml. of ethanol-water (1:1) to give 11.2 g. (67%) of colorless needles, o-(2-aminomethyl-1,4-cyclohexadienyl)acetic acid. M.p. 183° C.

IR: $\nu_{max}^{nuj}$ 1630, 1520, 1380, 1356 cm$^{-1}$.
NMR: $\delta$D$_2$O+K$_2$CO$_3$ 2.72

(4H, s, H$_2$C ), 3.01 (2H, s, C$\underline{H}_2$CO), 3.20 (2H, s, C$\underline{H}_2$-N), 5.78 (2H, s, $\underline{H}$>C=).

Anal. Calcd. for C$_9$H$_{13}$NO$_2$: C, 64.65; H, 7.84; N, 8.38. Found: C, 64.77; H, 8.06; N, 8.44.

Improved Procedure for the Preparation of α-(2-aminomethyl-1,4-cyclohexadienyl)-acetic acid

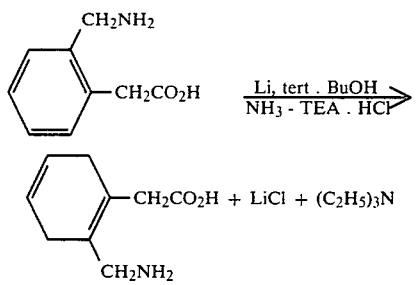

The procedure used by Welch, Dolfini and Giarrusso in U.S. Pat. No. 3,720,665 (Example 1) to make D-2-amino-2-(1,4-cyclohexadienyl)acetic acid was adapted. A solution of 830 ml. of distilled liquid ammonia was dried with 40 mg. of lithium under an argon atmosphere. To this stirred solution was added 11.0 g. (0.07 mole) of 2-aminomethylphenylacetic acid and 340 ml. of tert. butyl alcohol. A total of 1.6 g. (0.225 mole) of lithium was added to the vigorously stirred solution over a period of 2 hours. The grey mixture was then treated with 35 g. (0.215 mole) of triethylamine (TEA) hydrochloride and stirred overnight at room temperature for 18 hours. The tert. butyl alcohol was removed at 40° (15 mm.) to yield a white residue which was dried in vacuo over P$_2$O$_5$ overnight. The solid was dissolved in 30 ml. of 1:1 methanol-water and added with stirring to 3.5 l. of 1:1 chloroform-acetone at 5°. The mixture was stirred for 20 min. and the amino acid, α-(2-aminomethyl-1,4-cyclohexadienyl)acetic acid, was collected and dried for 16 hours in vacuo over P$_2$O$_5$ to yield 6.3 g. (58%) of white crystals, m.p. 190° decomp. The IR and NMR spectra were consistent for the structure.

A solution of 19.31 g. (0.135 m) of tert.butoxycarbonylazide in 152 ml. of tetrahydrofuran (THF) was added to a stirred solution of 14.89 g. (0.09 m) of 2-aminomethyl-1,4-cyclohexadienylacetic acid and 7.20 g. (0.18 m) of sodium hydroxide in 281 ml. of water. The solution was stirred for 18 hr. at 25° and then filtered thru diatomaceous earth (Super-cel). The THF was removed at 40° (15 mm) and the residual solution was washed with ether (2×175 ml.) and acidified with 6 N hydrochloric acid (HCl). The mixture was stirred in an ice-bath and the precipitate was collected and dried for 18 hr. in vacuo over P$_2$O$_5$ at 25° to yield 17.3 g. (72.6%) of 2-(tert.-butoxycarbonylaminomethyl)-1,4-cyclohexadienylacetic acid as a white powder. The IR and NMR spectra were consistent for the structure.

Preparation of 3-Aminomethyl-2-thiophene Acetic Acid

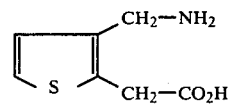

(A) Thiophene-3-carboxaldehyde Dimethyl Acetal (2a)

A mixture of thiophene-3-carboxaldehyde[1] (322 g., 2.9 moles), trimethoxymethane (636 g., 6 moles) and IR-120 resin (H+, 6 g.) in methanol (200 ml.) was refluxed over a period of 4 hours. The resin was removed and the filtrate was evaporated under reduced pressure to give a colorless oil which was distilled under reduced pressure. Yield 423 g. (94%), b.p. 90°–95° C. 13 mmHg.
[1] S. Gronowitz, Arkev, kemi., 8, 411 (1955).

ir: $\nu_{max}^{liq}$ 3150, 1045, 1025 cm$^{-1}$
nmr: $\delta_{ppm}^{neat}$ 3.21 (6H, s, OCH$_3$), 5.43

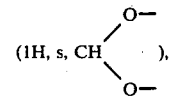

7.0–7.4 (3H, m, thiophene-$\underline{H}$)

B. 2-Formylthiophene-3-carboxaldehyde Dimethylacetal (3a)

To a stirred solution of 2a (423 g., 2.68 moles) in anhydrous ether (1 L) was added dropwise in 1 hour a freshly prepared solution of n-butyllithium (27 moles) in ether keeping a gentle reflux under dry N$_2$. Reflux being continued for 0.5 hour, a solution of DMF (dimethylformamide) (432 g., 6 moles) in anhydrous ether (0.8 L) was added dropwise to the mixture over a period of 0.75 hour with vigorous stirring. After the complete addition the mixture was stirred overnight, poured onto crushed ice (1 Kg.) with stirring and allowed to rise to room temperature. The organic layer was separated and the water layer was saturated with NaCl and extracted thoroughly with ether (2×200 ml.). The ether extracts were combined, dried over MgSO$_4$ and concentrated. The residue was distilled under reduced pressure and the pale yellow oil was collected at 100°–125° C., 0.7 mmHg. Yield, 277 g. (56%).
ir: $\nu_{max}^{liq}$ 3110, 1660, 1100 cm$^{-1}$.
nmr: $\delta_{ppm}^{neat}$ 3.40 (6H, s, OCH$_3$), 5.86

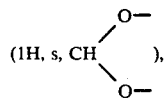

7.27 (1H, d, J=6Hz, thiophene-H$\beta$), 7.81 (1 H, d-d, J=1.5 and 6Hz, thiophene-Hα), 10.34 (1H, d, J=1.5 Hz, —CHO).

(C) 1-Methylsulfinyl-1-methylthio-2-(3-carboxaldehyde-ethyleneacetal-2-thienyl)ethylene (4b)

Preparation of 4b was carried out according to the procedure similar to that reported by K. Ogura et al.[4]. Triton B (40% in methanol, 2 ml. in THF (tetrahydrofuran) (5 ml.) was added to a solution of methyl methylthiomethyl sulfoxide[2] (2.5 g., 20 m. moles) and 2-formyl-3-thiophenecarboxaldehyde ethylene acetal[3] (3b). The mixture was refluxed for about one hour and concentrated under reduced pressure.

[2] K. Ogura, et al., Bull. Chem. Soc. (Japan), 45, 2203 (1972)
[3] D. W. McDowell et al., J. Org. Chem. 31, 3592 (1966)
[4] K. Ogura, et al., Tetrahedron Letters, 1383 (1972). The residue was dissolved in benzene (150 ml) and extracted with water (3×20 ml). The organic layer was dried over MgSO₄ and evaporated to dryness under reduced pressure. The residue was column-chromatographed on silica gel (80 g) eluting with benzene (500 ml) and chloroform (500 ml) successively. From the chloroform eluate 4.9 g (85%) of the product 4b was isolated as a pale yellow oil.

ir: $\nu_{max}^{liq}$ 3110, 1600 cm$^{-1}$.

nmr: $\delta_{ppm}^{CDCl_3}$ 2.42 (3H, s, S—CH$_3$), 2.78 (3H, s, SO—CH$_3$), 4.15 (4H, m, CH$_2$CH$_2$—), 6.12

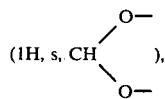

(1H, s, CH⟨O—/O—⟩), 7.34 (1H, d, J=4.5Hz, thiophene-H$\beta$), 7.40 (1H, d, J=4.5Hz, thiophene-H$\alpha$), 8.28 (1H, s, —CH=).

The semicarbazone of 4 was prepared by a usual manner and crystallized from ethanol-DMF. M.p. 212°–213° C.

Anal. Calcd. for C$_{10}$H$_{13}$N$_3$O$_2$S$_2$: C, 39.58; H, 4.32; N, 13.85; S, 31.70. Found: C, 39.46; H, 4.24; N, 14.05; S, 31.63.

(D) 1-Methylsulfinyl-1-methylthio-2-(3-carboxaldehyde dimethylacetal-2-thienyl)ethylene (4a)

The compound 4a was prepared by the procedure similar to that for 4b. Triton B (40% in methanol, 50 ml) was added to a solution of methyl methylthiomethylsulfoxide (72 g., 0.58 mole) and 3a (108 g, 0.58 mole) in THF (300 ml) and the mixture was refluxed for 4 hours. Separation by column chromatography with silica gel (400 g) eluting with chloroform (5 L) gave 130.5 g (78%) of 4a as a pale yellow oil.

ir: $\nu_{max}^{liq}$ 3100, 1580, 1100, 1050$^{-1}$.

nmr: $\delta_{ppm}^{CCl_4}$ 2.42 (3H, s, S—CH$_3$), 2.70 (3H, s, SO—CH$_3$), 3.34 (6H, s, OCH$_3$), 5.56

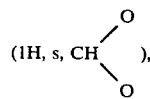

(1H, s, CH⟨O/O⟩), 7.20 (1H, d, J=6Hz, thiophene-H$\beta$), 7.40 (1H, d, J=6Hz, thiophene-H$\alpha$), 8.12 (1H, s, —CH=).

(E) Ethyl 3-formyl-2-thienylacetate[4] (5)

Dry hydrogen chloride (33 g) was absorbed in anhydrous ethanol (500 ml). To this solution 4a (130 g, 0.45 mole) was added and the mixture heated under reflux for 5 mins. The reaction mixture was diluted with water and evaporated under reduced pressure. The residue was extracted with benzene (2×100 ml) and the benzene extracts were combined, washed with water (50 ml), dried over MgSO₄ and evaporated to dryness. The oily residue was column-chromatographed on silica gel (400 g) eluting with chloroform (5 L). Fractions containing the desired product were combined and concentrated. The residual oil (60 g) was distilled under reduced pressure to afford 23 g (23%) of 5, boiling at 120°–126° C./1 mmHg.

ir: $\nu_{max}^{liq}$ 3110, 1730, 1670 cm$^{-1}$.

nmr: $\delta_{ppm}^{CDCl_3}$ 1.30 (3H, t, J=6Hz, —CH$_2$CH$_3$), 4.25 (2H, q, J=6Hz, —CH$_2$CH$_3$), 4.26 (2H, s, —CH$_2$CO), 7.25 (1H, d, J=5Hz, thiophene-H$\beta$), 7.48 (1H, d, J=5Hz, thiophene-H$\alpha$), 10.15 (1H, s, CHO).

The analytical sample of 5 was submitted as the 2,4-dinitrophenylhydrazone which was crystallized from chloroform. M.p. 178°–179° C.

ir: $\nu_{max}^{nujol}$ 1720, 1610, 1570 cm$^{-1}$.

Anal. Calcd. for C$_{15}$H$_{14}$N$_4$O$_6$S: C, 47.62; H, 3.73; N, 14.81; S, 8.47. Found: C, 47.33; H, 3.47; N, 14.77; S, 8.68.

According to the similar procedure 2.2 g (7.6 m moles) of the ethylene acetal 4b was treated with 1.1 g of dry hydrogen chloride in 800 ml of anhydrous ethanol to afford 5 which was purified by column chromatography on silica gel (30 g). Elution with chloroform gave 663 mg (44%) of 5 as a pale yellow oil.

(F) Ethyl 3-formyl-2-thienylacetate oxime (6)

Sodium carbonate (1.7 g, 16 m mole) was added to a solution of the aldehyde 5, (3.14 g, 16 m mole) and hydroxylamine hydrochloride (2.2 g, 32 m mole) in 50% aq. ethanol (40 ml) at 5° C. with stirring. The reaction mixture was warmed up to room temperature. After 2.5 hrs., the reaction mixture was concentrated under reduced pressure. The residue was extracted with benzene (3×50 ml). The benzene extracts were washed with water (10 ml), dried over MgSO₄, and evaporated under reduced pressure. Separation by column chromatography on silica gel (60 g) gave 2.7 g (80%) of colorless oil 6.

ir: $\nu_{max}^{liq}$ 3400, 1730, 1620 cm$^{-1}$.

nmr: $\delta_{ppm}^{Aceton-d_6}$ 1.23 (3H, t, J=7.5Hz, —CH$_2$CH$_3$), 4.01 (2H, s, —CH$_2$CO), 4.14 (2H, q, J=7.5Hz, —CH$_2$CH$_3$), 7.31 (2H, s, thiophene-H), 8.26 (1H, s, —CH=N), 10.15 (1H, s, NOH, disappeared by addition of D$_2$O).

(G) The δ-lactam of 3-aminomethyl-2-thienylacetic acid (7)

Method A: Catalytic reduction

A mixture of the oxime 6 (2.65 g, 12.4 m moles), 10% palladium on charcoal, dry hydrogen chloride (1.4 g, 37.2 m moles) in anhydrous ethanol (68 ml) was hydrogenated overnight under atmospheric pressure at room temperature. The catalyst was exchanged twice and the reaction was carried out over a period of 3 days. The catalyst was removed and the filtrate was concentrated under reduced pressure. To the residue was added water (10 ml) and the mixture washed with ethyl acetate (2×10 ml). The aqueous layer was adjusted to pH 9 with sodium carbonate, saturated with sodium chloride, and extracted with ethyl acetate (3×20 ml). The ethyl acetate extracts were dried over MgSO₄, treated with charcoal, and evaporated under reduced pressure. Recrystallization from ethyl acetate gave 417 mg (22%) of colorless needles 7 melting at 194°–195° C.

ir: $\nu_{max}^{KBr}$ 3200, 1650, 1480 cm$^{-1}$.

nmr: $\delta_{ppm}^{DMSO-d_6}$ 3.53 (2H, t, J=3 Hz, —CH$_2$CO—), 4.36 (2H, d-t, J=3, 1.5 Hz, changed to a triplet by addition of D$_2$O, J=3 Hz, CH$_2$N), 6.95 (1H, d, J=4.5

Hz, thiophene-Hβ), 7.45 (1H, d, J=4.5 Hz, thiophene-Hα), 8.0 (1H, m, disappeared by addition of D₂O, NH).

Anal. Calcd. for C₇H₇NOS: C, 54.88; H, 4.61; N, 9.14; S, 20.93. Found: C, 55.04; H, 4.45; N, 9.13; S, 20.50.

Method B: Zn-dust reduction

To a solution of the oxime 6 (18.3 g, 86 m moles) in acetic acid (200 ml), zinc dust (17 g, 258 m moles) was added portionwise over a period of 1 hr. at 40°–50° C. with vigorous stirring. The reaction mixture was stirred overnight at room temperature and heated at 60° C. for 4 hours. The contents were filtered and the filtrate was concentrated under reduced pressure. To the residual oil was added water (100 ml) and the mixture washed with ether (2×50 ml). The aqueous solution was layered with ethyl acetate (100 ml) and adjusted to pH 10 with sodium carbonate. The precipitate was filtered off. The filtrate was extracted with ethyl acetate. The ethyl acetate extracts were washed with water (10 ml), dried over MgSO₄, and evaporated under reduced pressure. The residual solid was triturated with benzene. Crystallization from ethyl acetate gave 2.7 g (21%) of the lactam 7 which was identical to Method A in the IR and the NMR spectra.

H. 3-Aminomethyl-2-thienylacetic acid (8)

A mixture of the lactam 7 (2.88 g, 18.8 m moles) and 6 N hydrochloric acid (50 ml) was heated under reflux for 3 hrs. The reaction mixture was concentrated under reduced pressure. To the residue was added water (20 ml) and the mixture treated with charcoal and evaporated under reduced pressure. The trituration of the residue with THF gave the amino acid 8 hydrochloride (3.72 g, 95%; m.p. 171°–172° C.; ir (KBr) cm⁻¹: 3450, 3000, 1700, 1200; nmr (D₂O)ppm: 4.80 (2H, s, —CH₂CO), 4.27 (2H, s, CH₂—N), 7.26 (1H, d, J=6 Hz, thiophene-Hβ), 7.53 (1H, d, J=6 Hz, thiophene-Hα). The hydrochloride (3.71 g, 17.9 m moles) was dissolved in water (10 ml) chromatographed on a column of IR-120 (H, 30 ml) and developed successively with water (100 ml) and 5 N-NH₄OH (2 L). The ammonia eluate was evaporated to dryness. The residue was crystallized from aqueous acetone to give 3.0 g (98%) of 8, m.p. 223°–225° C.

ir: $\nu_{max}^{KBr}$ 3000, 1620, 1520 cm⁻¹.

nmr: $\delta_{ppm}^{D2O\text{-}Na2CO3}$ 3.20 (2H, s, —CH₂CO), 4.13 (2H, s, CH₂N), 7.04 (1H, d, J=6 Hz, thiophene-Hβ), 7.30 (1H, d, J=6 Hz, thiophene-Hα).

Anal. Calcd. for C₇H₉NO₉S: C, 49.10; H, 5.30; N, 8.18; S, 18.73. Found: C, 48.53: h, 5.22; N, 7.98; S, 18.97.

I. 3-t-Butoxycarbonylaminomethyl-2-thienylacetic acid (9)

A mixture of 3-aminomethyl-2-thienylacetic acid 8 (3.1 g, 18 m. moles) and triethylamine (8 g. 80 m moles) in 50% aqueous acetone (80 ml) was added dropwise t-butoxycarbonyl azide (5.7 g, 40 m moles) over a period of 20 mins. at 0° C. with vigorous stirring. The reaction mixture was stirred overnight at room temperature and concentrated under reduced pressure. The concentrate was washed with ether (2×20 ml), adjusted to pH 2 with conc. HCl and extracted with ethyl acetate (2×50 ml). The ethyl acetate extracts were washed with saturated aqueous sodium chloride, dried over MgSO₄, treated with charcoal and evaporated under reduced pressure. The residue was triturated with n-hexane and crystallized from n-hexane and benzene to give 4.5 g (92%) of colorless needles 9, melting at 62°–63° C.

ir: $\nu_{max}^{nujol}$ 3350, 1700 cm⁻¹.

nmr: $\delta_{ppm}^{CDCl_3}$ 1.43 (9H, s, BOC-H), 3.27 (2H, s, CH₂CO), 4.16 (2H, d, J=6 Hz, CH₂—N, a singlet when D₂O was added), 5.00 (1H, br, —NH—, disappeared by addition of D₂O), 6.30 (1H, broad s, —COOH, disappeared by addition of D₂O), 6.86 (1H, d, J=6 Hz, thiophene-Hβ), 7.06 (1H, d, J=6 Hz, thiophene-Hα).

Anal. Calcd. for C₁₂H₁₇NO₄S: C, 52.89; H, 6.29; N, 5.14; S, 11.77. Found: C, 53.30; H, 6.39; N, 5.13; S, 11.72.

Preparation of 2-N-Methylaminomethyl-4-methoxy-(and 4-hydroxy-)phenylacetic Acids

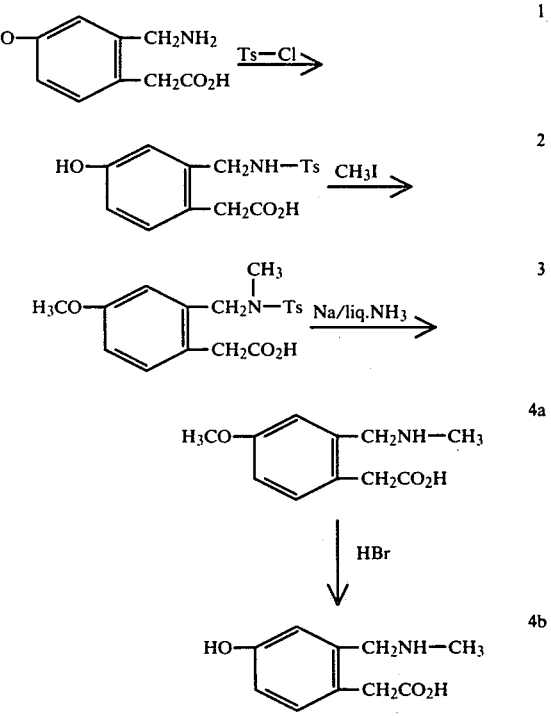

2-N-Tosylaminomethyl-4-hydroxyphenylacetic Acid (2)

To a solution of 14.56 g. (0.08 mol.) of 2-aminomethyl-4-hydroxyphenylacetic acid (1) (U.S. Pat. No. 3,823,141) and 13 g. (0.32 mol.) of sodium hydroxide in 200 ml. of water was added dropwise with stirring at 65°–70° C. a solution of 18.5 g. (0.097 mol.) of p-toluenesulfonyl chloride in 50 ml. of dry ether and the mixture was kept at the same temperature for one hour. The mixture being cooled, the aqueous layer was separated, washed with ether (2×50 ml.), acidified with 6 N HCl and extracted with 400 ml. of ethyl acetate. The extract was washed with water and a saturated aqueous NaCl solution, dried with Na₂SO₄ and treated with active carbon (1 g.). The filtrate was concentrated to dryness and the residue was crystallized from ethyl acetate to give 11.0 g. (40.5%) of 2 melting at 212°–215° C.

ir: $\nu_{max}^{KBr}$ 3240, 1700, 1380, 1330, 1150 cm⁻¹ uv: $\lambda_{max}^{1\%K2CO3}$ 230 nm (ε: 7,750)

nmr: $\delta_{ppm}{}^{DMSO\text{-}d6}$ 2.47 (3H, s, Ar—CH$_3$), 3.60 (2H, s, CH$_2$CO), 3.93 (2H, d, J=6.0 Hz, CH$_2$N), 6.6–8.2 (7H, m, phenyl-$\underline{H}$).

2-(N-Methyl-N-tosylamino)methyl-4-methoxyphenylacetic Acid (3)

A mixture of 11 g. (0.033 mol.) of 2, 10.3 ml. (0.17 mol.) of methyl iodide and 9.2 g. (0.24 mol.) of sodium hydroxide in 100 ml. of water was heated at 80°–90° C. for 45 minutes in a sealed tube with occasional shaking. The mixture was washed with ethyl acetate (30 ml.) and the water layer was acidifed with 6 N HCl and extracted with ethyl acetate (3×30 ml.). The combined extracts were washed with water (30 ml.) and a saturated aqueous NaCl solution (30 ml.) treated with active carbon (1 g.) and dried over Na$_2$SO$_4$. The filtrate was evaporated to dryness and the residue was crystallized from benzene to give 8 g. (66.5%) of the N,O-dimethyl derivative 3 melting at 146°–150° C.

ir: $\nu_{max}{}^{KBr}$ 1690, 1500, 1340, 1280, 1150 cm$^{-1}$.
uv: $\lambda_{max}{}^{EtOH}$ 229 nm ($\epsilon$: 20500), 278 nm ($\epsilon$: 2400).
nmr: $\delta_{ppm}{}^{DMSO\text{-}d6}$ 2.52 (3H, s, N—CH$_3$), 2.47 (3H, s, Ar—CH$_3$), 3.67 (2H, s, CH$_2$CO), 3.74 (3H, s, OCH$_3$), 4.10 (2H, s, CH$_2$N), 6.7–7.8 (7H, m, Ar-$\underline{H}$), 11.5 (1H, br-s, COOH).
Anal. Calc'd. for C$_{18}$H$_{21}$NO$_5$S: C, 59.49; H, 5.82; N, 3.84; S, 8.82. Found: C, 59.48; H, 5.68; N, 3.37; S, 9.22.

2-N-Methylaminomethyl-4-methoxyphenylacetic Acid (4a)

To a solution of liquid ammonia (300 ml.) was added 9.4 g. (0.026 mol.) of 3 at −50° C. and the mixture was stirred until a clear solution was obtained at the same temperature. To the solution was added 3.3 g. (0.14 g. atom) of Na in small pieces at −40° C. and the mixture was stirred for 2 hours. Ammonia was evaporated and the residue was dissolved in 100 ml. of water carefully. To the solution was added 100 ml. of Amberlite IR-C 50 (ammonium type) and the mixture was stirred for 30 minutes to room temperature. The resin was removed and the filtrate was treated with barium acetate until no more precipitate was observed. The precipitate was filtered off and the filtrate was chromatographed with a column of IR-120 ion-exchange resin (H$^+$, 100 ml.) by eluting with 5–10% ammonia. The eluate (2 L) containing the desired product was evaporated to dryness below 50° C. and the residue was triturated with acetone to give 4.4 g. (81%) of 4a, m.p. 225°–227° C.
ir: $\nu_{max}{}^{KBr}$ 1590, 1380, 1260, 1035 cm$^{-1}$.
nmr: $\delta_{ppm}{}^{D2O}$ 2.77 (3H, s, N—CH$_3$), 3.6 (2H, s, CH$_2$CO), 3.87 (3H, s, OCH$_3$), 4.18 (2H, s, CH$_2$N), 6.8–7.4 (3H, m, phenyl-$\underline{H}$).

2-N-Methylaminomethyl-4-hydroxyphenylacetic Acid (4b)

A mixture of 2.9 g. (0.014 mol.) of 4a in 30 ml. of 48% hydrobromic acid was refluxed for 5 hours and the solution was evaporated to dryness. The residue was dissolved in 50 ml. of water. The solution was chromatographed on a column of Amberlite IR-120 (H$^+$, 50 ml.) eluting with 5–10% ammonia. The eluate was collected in 250 ml. fractions. Fractions containing the product were combined and evaporated to dryness below 50° C. The residue was triturated with acetone to give 1.3 g. (48.5%) of 4b, which was crystallized from 80% ethanol. M.p. 218°–221° C.
ir: $\nu_{max}{}^{KBr}$ 2000–3400, 1610, 1540, 1460, 1380, 1270 cm$^{-1}$.

uv: $\lambda_{max}{}^{1\%K2CO3}$ 243 nm ($\epsilon$: 4700), 297 nm ($\lambda$: 1350).
nmr: $\delta_{ppm}{}^{D2O+NaOH}$ 2.64 (3H, s, N—CH$_3$), 3.47 (2H, s, CH$_2$CO), 3.94 (2H, s, N—CH$_2$), 6.5–7.2 (3H, m, phenyl-$\underline{H}$).
Anal. Calc'd. for C$_{10}$H$_{13}$NO$_3$: C, 61.53; H, 6.71; N, 7.17. Found: C, 61.44; H, 6.81; N, 7.20.

2-N-t-Butoxycarbonyl-N-methylaminomethyl-4-methoxyphenylacetic Acid (5, R=CH$_3$)

A mixture of 1.05 g. (5 m.mol.) of 4a, 1.43 g. (6 m.mol.) of t-butyl 4,6-dimethylpyrimidin-2-ylthiolcarbonate and 1.4 ml. of triethylamine in 40 ml. of 50% THF was stirred at room temperature for 20 hours. Most of the THF was evaporated and the resulting aqueous solution (ca. 20 ml.) was washed with ether. The water layer was acidified with 6N HCl and extracted with ether (3×10 ml.). The ethereal extracts were washed with water (10 ml.) and a saturated aqueous NaCl solution (10 ml.), treated with a small amount of active carbon and dried over Na$_2$SO$_4$. The filtrate was evaporated to dryness to give 1.0 g. (77.5%) of 5 (R=CH$_3$) as an oil.
nmr: $\delta_{ppm}{}^{CDCl3}$ 1.47 (9H, s, BOC-$\underline{H}$), 2.77 (3H, s, N—CH$_3$), 3.60 (2H, s, CH$_2$CO), 3.79 (3H, s, O—CH$_3$), 4.49 (2H, s, CH$_2$N), 6.1–7.3 (3H, m, phenyl-$\underline{H}$).

2-N-t-Butoxycarbonyl-N-methylaminomethyl-4-hydroxyphenylacetic Acid (5, R=H)

A mixture of 1 g. (4.78 m.mol.) of 4b, 1.5 g. (6.3 m.mol.) of t-butyl 4,6-dimethylpyrimidin-2-ylthiolcarbonate and 2.1 ml. of triethylamine in 50 ml. of 50% aqueous THF solution was stirred at room temperature for 20 hours. The mixture was concentrated to 20 ml. under reduced pressure. The concentrate was washed with ether (10 ml.), acidified with 6N HCl and extracted with ethyl acetate (2×100 ml.). The combined extracts were washed with water (30 ml.) and a saturated aqueous NaCl solution (2×30 ml.), treated with a small amount of active carbon and dried over anhydrous Na$_2$SO$_4$. The filtrate was evaporated to dryness to give 1.3 g. (92%) of 5 (R=H) as an oil.
ir: $\nu_{max}{}^{liq}$ 3000–3600, 1670, 1260, 1150 cm$^{-1}$.
nmr: $\delta_{ppm}{}^{CDCl3}$ 1.44 (9H, s, C(CH$_3$)$_3$), 2.73 (3H, s, N—CH$_3$), 3.54 (2H, s, CH$_2$CO), 4.38 (2H, s, CH$_2$N), 6.5–7.3 (3H, m, phenyl-$\underline{H}$).

Preparation of Ortho-N-methylaminomethyl-phenylacetic Acid

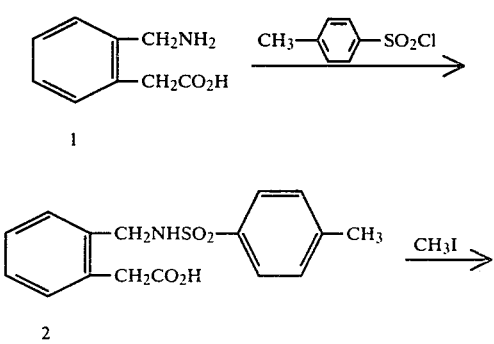

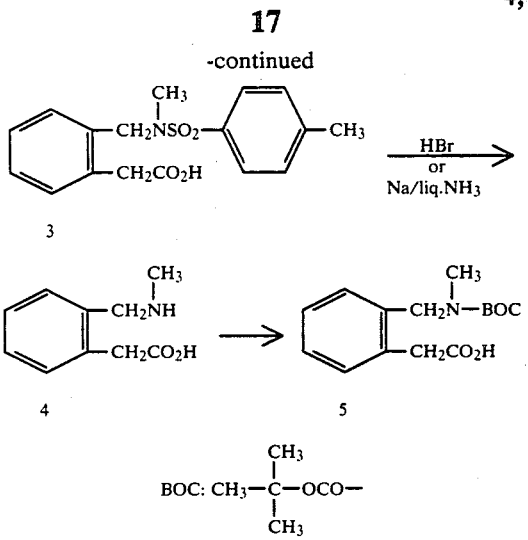

BOC: $CH_3-\underset{\underset{CH_3}{|}}{\overset{\overset{CH_3}{|}}{C}}-OCO-$ o-(p-Toluenesulfonylaminomethyl)phenylacetic Acid (2)

To a stirred solution of o-aminomethylphenylacetic acid hydrochloride (7.50 g., 37 m.mol.) and sodium hydroxide (4.74 g., 118 m.mol.) in water (100 ml.) was added p-toluenesulfonyl chloride (7.64 g., 40 m.mol.) in portions at 60° C. The mixture was stirred for 1 hour at the same temperature and acidified with hydrochloric acid. The mixture was extracted with ethyl acetate (4×50 ml.). The combined extracts were washed with water, treated with a small amount of carbon and dried. The solvent was evaporated under reduced pressure and the residue crystallized from ethyl acetate to afford 2 as colorless prisms. Yield, 9.84 g. (84%). M.p. 155°-156° C.

ir: $\nu_{max}^{nuj}$ 3300, 1705, 1335, 1170 cm$^{-1}$.

nmr: $\delta_{ppm}^{DMSO-d6}$ 2.38 (3H, s, CH$_3$), 3.65 (2H, s, CH$_2$CO), 3.97 (2H, d, J=5 Hz, CH$_2$N), 7.1-8.2 (9H, m, phenyl-H & NH).

Anal. Calc'd. for C$_{16}$H$_{17}$NO$_4$S: C, 60.17; H, 5.37; N, 4.39; S, 10.10. Found: C, 60.11, 60.15; H, 5.43, 5.40; N, 4.28, 4.30; S, 9.72, 9.80.

o-(N-p-Toluenesulfonyl-N-methylaminomethyl)-phenylacetic Acid (3)

A mixture of 2 (9.0 g., 28 m.mol.) sodium hydroxide (6.0 g.) and methyl iodide (6 ml.) in water (60 ml.) was heated in a sealed tube for 30 minutes at 70° C. After cooling, the reaction mixture was acidified with hydrochloric acid to separate pale yellow precipitate which was crystallized from ethyl acetate-n-hexane to give colorless prisms, 3. Yield, 8.5 g. (91%). M.p. 162°-163° C.

ir: $\nu_{max}^{KBr}$ 2700-2300, 1700, 1600, 1345, 1200, 925 cm$^{-1}$.

nmr: $\delta_{ppm}^{D2O+KOH}$ 2.37 (3H, s, CH$_3$), 2.49 (3H, s, CH$_3$), 3.80 (2H, s, CH$_2$CO), 4.18 (2H, s, CH$_2$N), 7.0-8.0 (8H, m, phenyl-H).

Anal. Calc'd. for C$_{17}$H$_{19}$NO$_2$: C, 61.24; H, 5.74; N, 4.20; S, 9.61. Found: C, 61.31, 61.36; H, 5.73, 5.71; N, 4.51, 4.29; S, 9.63, 9.55.

N-Methylaminomethylphenylacetic Acid (4)

Method A (using hydrobromic acid)—A mixture of 28.6 g. (0.086 mol.) of 3 and 20 g. (0.213 mol.) of phenol in 260 ml. of 48% hydrobromic acid was refluxed for 30 minutes. The mixture was cooled, diluted with the same volume of water and washed with ethyl acetate (2×50 ml.). The aqueous layer was evaporated to dryness in diminished pressure to give an oil which was chromatographed on a column of Amberlite IR-120 (H$^+$ form, 200 ml.) eluting with 5% ammonium hydroxide solution. The eluate (2.5 l.) was collected and evaporated to dryness under reduced pressure. The residue was triturated with acetone and crystallized from ethanol to afford 6.7 g. (43.5%) of 4 as colorless needles, melting at 168°-170° C. (dec.).

Method B (using metallic sodium in liquid ammonia)—To a mixture of 3 (35 g., 0.105 mol.) in liquid ammonia (1000 ml.) was added 13.3 g. (0.578 atom) of sodium in small pieces under vigorous stirring over a period of 2 hours. The ammonia was evaporated with stirring on a water-bath in a well-ventilated hood and finally under reduced pressure to remove it completely. The residue was dissolved in ice water (400 ml.) and the solution was stirred with ion-exchange resin IRC-50 (H$^+$ form, 400 ml.) for 0.5 hour at room temperature. The resin was filtered off and to the filtrate was added an aqueous 1 M solution of barium acetate until no more precipitate was formed (ca 50 ml. of the barium acetate solution was required). The mixture was filtered and the filtrate was chromatographed on a column of IR-120 (H$^+$ form, 400 ml.) as in Method A to give 13.6 g. (72%) of 4.

o-(N-methyl-N-t-butoxycarbonylaminomethyl)-phenylacetic Acid (5)

t-Butyl 4,6-dimethylpyrimidin-2-ylthiolcarbonate (11 g., 0.048 mol.) was added in one portion to a mixture of 4 (7.2 g., 0.04 mol.) and 1,1,3,3-tetramethylguanidine (6.9 g., 0.06 mol.) in 50% aqueous THF and the mixture was stirred overnight at room temperature. The THF being evaporated under reduced pressure, the aqueous solution was acidified to pH 2 with dil. hydrochloric acid and extracted with ethyl acetate (2×20 ml.). The combined extracts were washed with water, treated with a small amount of active carbon and evaporated under diminished pressure. The residue was triturated with hexane and crystallized from n-hexane-ether to afford 9.2 g. (83%) of 5 as colorless prisms. M.p. 96°-98° C.

ir: $\nu_{max}^{KBr}$ 1730, 1630, 1430, 1830, 1250 cm$^{-1}$.

nmr: $\delta_{ppm}^{CDCl3}$ 1.49 (9H, s, t-butyl), 2.78 (3H, s, N—CH$_3$), 3.72 (2H, s, CH$_2$CO), 4.25 (2H, s, CH$_2$N), 7.28 (4H, s, phenyl), 9.83 (1H, s, —COOH).

Anal. Calc'd. for C$_{15}$H$_{21}$NO$_4$: C, 64.50; H, 7.58; N, 5.01. Found: C, 64.69; H, 7.66; N, 4.89.

Preparation of 3-N-methylaminomethyl-2-thienylacetic Acid

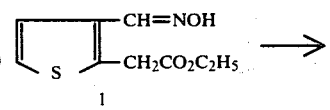

1

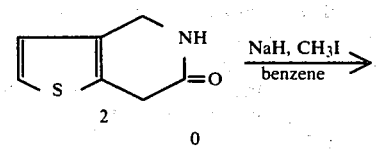

2

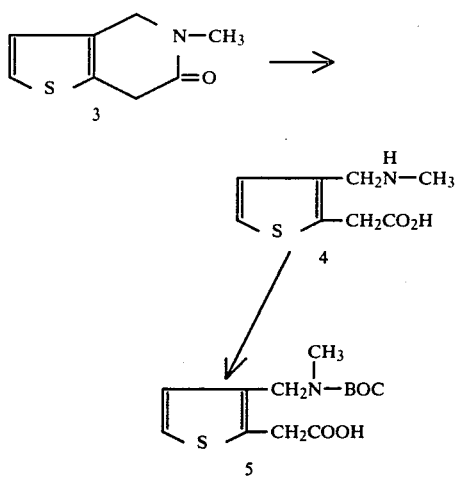

3-Aminomethyl-2-thienylacetic Acid δ-lactam (2)

Glacial acetic acid (140 ml.) was added dropwise with stirring to a mixture of 2-ethoxycarbonylmethyl-thiophene-3-carboxaldehyde oxime (1) (41 g., 0.19 mole) and zinc dust (65.4 g., 1 mole) in methanol, and the mixture was stirred under reflux for 4 hours. The mixture was cooled and insolubles were removed by filtration and washed with methanol (3×50 ml.). The filtrate was combined with the washings and evaporated in vacuo to dryness, the residue being extracted with methanol (5×100 ml.). The methanol extracts were combined and evaporated under reduced pressure. To the residue was added water (50 ml.) and the mixture was adjusted to pH 10 with $Na_2CO_3$ and extracted with chloroform (3×100 ml.). The combined chloroform extracts were washed with water (10 ml.), dried over $MgSO_4$, and evaporated under reduced pressure. The residual oil (30 g.) was triturated with hot benzene (150 ml.). The colorless needles were collected by filtration and recrystallized from ethyl acetate to give the lactam 2 (7.7 g., 26%), melting at 195°–196° C.

UV: $\lambda_{max}^{MeOH}$ 232 nm (ε, 6500)

Anal. Calc'd. for $C_7H_7NOS$: C, 54.88; H, 4.61; N, 9.14; S, 20.93. Found: C, 55.04; H, 4.45; N, 9.13; S, 20.50.

3-N-Methylaminomethyl-2-thienylacetic Acid δ-lactam (3)

To a suspension of sodium hydride (50% in paraffin, 1.82 g., 38 m.moles) in absolute benzene (500 ml.) was added the lactam 2 (4.85 g., 32 m.moles) with stirring under nitrogen atmosphere and the mixtures was refluxed for 2 hours. Methyl iodide (22.7 g., 160 m.moles) was added in one portion at room temperature and the mixture was again refluxed for 2 hours. ice-water (50 g.) was added to the mixture and organic layer was separated. The aqueous layer was extracted successively with benzene (2×50 ml.) and chloroform (50 ml.). The extracts were combined and dried on $MgSO_4$. The solvent was evaporated under reduced pressure. To the residue was added a hot mixture of benzene-n-hexane (1:1, 100 ml.) to recover 2 as needles (2.02 g., 42%). The filtrate was evaporated and the residue was crystallized from benzene-n-hexane to afford colorless plates 3. Yield: 2.7 g. (51%). M.p. 98°–100° C.

ir: $\nu_{max}^{nujol}$ 1620 cm$^{-1}$.

nmr: $\delta_{max}^{CHCl_3}$ 3.15 (3H, s, N—CH$_3$), 3.72 (2H, t, J=3 Hz, CH$_2$CO), 4.53 (2H, t, J=3 Hz, —CH$_2$—N), 6.87 (1H, d, J=4.5 Hz, thiophene-H$\beta$), 7.30 (1H, d, J=4.5 Hz, thiophene-H$\alpha$.

uv: $\lambda_{max}^{MeOH}$ 232 nm (ε, 6700)

Anal. Calc'd. for $C_8H_9NOS$: C, 57.46; H, 5.42; N, 8.38; S, 19.17. Found: C, 57.56; H, 5.26; N, 8.31; S, 19.13.

3-(N-Methylaminomethyl)-2-thienylacetic Acid (4)

A mixture of the lactam 3 (3.5 g., 21 m.moles) and 6 N HCl (100 ml.) was heated under reflux for 12 hours. The mixture was treated with carbon and concentrated to dryness under reduced pressure. The residual oil was dissolved in water (10 ml.) and chromatographed on a column of IR-120 (H$^+$, 50 ml.). The column was eluted with water (200 ml.) and 5 N, NH$_4$OH (3 L.). The amino acid 4 (3.0 g., 77%) was isolated by evaporation of the ammonia eluates followed by crystallization from aqueous acetone. M.p. 181°–182° C.

ir: $\nu_{max}^{KBr}$ 1570, 1360 cm$^{-1}$.

nmr: $\delta_{ppm}^{D_2O}$ 2.21 (3H, s, N—CH$_3$), 3.80 (2H, s, CH$_2$CO), 4.20 (2H, s, CH$_2$—N), 7.19 (1H, d, J=6 Hz, thiophene-H$\beta$), 7.46 (1H, d, J=6 Hz, thiophene-H$\alpha$).

uv: $\lambda_{max}^{H_2O}$ 237 nm (ε, 7600)

Anal. Calc'd. for $C_8H_{11}NO_2S$: C, 51.87; H, 5.99; N, 7.56; S, 17.31. Found: C, 51.67; H, 6.50; N, 7.28; S, 16.69.

3-(N-t-butoxycarbonyl-N-methylaminomethyl)-2-thienylacetic Acid (5)

To a mixture of 3-N-methylaminomethyl-2-thienylacetic acid 4 (2.7 g., 14.6 m.moles) and triethylamine (6 g., 60 m.moles) in 50% aqueous acetone (60 ml.) was added dropwise t-butoxycarbonyl azide (4.2 g., 29.2 m.moles) over a period of 20 minutes at 0° C. with vigorous stirring. The reaction mixture was stirred overnight at room temperature and concentrated under reduced pressure. The concentrate was washed with ether (2×20 ml.), adjusted to pH 2 with concentrated HCl and extracted with ethyl acetate (2×50 ml.). The ethyl acetate extracts were washed with a saturated aqueous NaCl solution, dried on MgSO$_4$, treated with charcoal and evaporated under reduced pressure. The residue was triturated with n-hexane and crystallized from n-hexane-benzene to give 3.68 g. (88%) of colorless needles 5 melting at 82°–83° C.

ir: $\nu_{max}^{nujol}$ 1730, 1640 cm$^{-1}$.

nmr: $\delta_{ppm}^{CDCl_3}$ 1.47 (9H, s, BOC-H), 2.78 (3H, s, N—CH$_3$), 3.87 (2H, s, CH$_2$—CO), 4.48 (2H, s, CH$_2$—N), 6.91 (1H, d, J=6 Hz, thiophene-H$\beta$), 7.20 (1H, d, J=6 Hz, thiophene-H$\alpha$), 10.63 (1H, s, CO$_2$H, disappeared by addition of D$_2$O).

Anal. Calc'd. for $C_{13}H_{19}NO_4S$: C, 54.72; H, 6.71; N, 4.91; S, 11.24. Found: C, 54.91; H, 6.85; N, 4.92; S, 11.19.

The use of an "en-amine" blocking group with a prospective 7-side chain containing a free amino group prior to acylation of a nucleus such as II herein is well known as from U.S. Pat. Nos. 3,223,141, 3,813,390; 3,813,391; 3,823,141 and Belgium Pat. No. 773,773.

Sodium 2-[N-(1-carbethoxypropen-2-yl)aminomethyl]-1,4-cyclohexadienyl acetate (4)

To a stirred solution of 460 mg. (0.02 g. atom) of metallic sodium in 100 ml. of absolute EtOH was added 3.34 g. (0.02 mole) of 2-aminomethyl-1,4-cyclohexadienylacetic acid and 3.1 g. (0.024 mole of ethyl acetoacetate and the mixture was heated to reflux for 4 hours with stirring. The hot reaction mixture was filtered and the filtrate was allowed to keep cold overnight to give 2.0 g. of colorless needles 4 melting at 264° C. The additional product (3.3 g.) was obtained by concentration of the mother liquid. The total yield was 5.3 g. (88%).

IR: $\nu_{max}^{nuj}$ 3300, 1635, 1600, 1570, 1300, 1275, 1170, 1090 cm$^{-1}$.

NMR: $\delta_{ppm}^{D2O}$ 1.23 (3H, t, 7 Hz, CH$_2$C$\underline{H}_3$), 1.96 & 2.25 (3H, s, C=C—C$\underline{H}_3$, cis & trans), 2.70

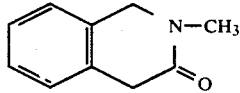

(4H, s, H$_2$C     ), 3.04 (2H, s, C$\underline{H}_2$CO), 3.66 & 3.95 (2H, s, C$\underline{H}_2$—N, cis & trans), 4.07 (2H, q, 7 Hz, C$\underline{H}_2$CH$_3$), 4.45 & 4.56

(1H, s, —$\overset{H}{=}$, cis & trans), 5.76 (2H, s, [cyclohexadiene H]).

Anal. Calcd. for C$_{15}$H$_{20}$NO$_4$Na: C, 59.79; H, 6.69; N, 4.64. Found: c, 59.69; H, 6.76; N, 4.75.

2-t-Butoxycarbonylaminomethyl-4-hydroxyphenylacetic acid is prepared, for example, according to U.S. Pat. No. 3,823,141.

o-(N-methylaminomethyl)phenylacetic acid δ-lactam

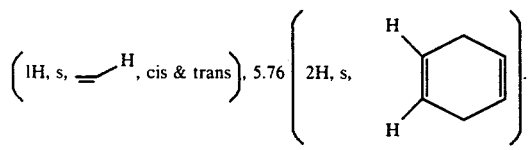

Sodium hydride (57% in paraffin, 4.3 g.; 0.11 mol.) was washed with dry n-hexane and suspended in dry benzene (100 ml.). To the suspension was added a solution of o-aminomethylphenylacetic acid δ-lactam (U.S. Pat. No. 3,796,716) (14.7 g., 0.1 mol.) in dry benzene or xylene (200 ml.) with stirring under a nitrogen atmosphere. The mixture was refluxed for one hour and cooled to room temperature. To the mixture was added methyl iodide (18 ml.) in one portion and the mixture was refluxed again for 1.5 hours. The reaction mixture was cooled to room temperature and poured into ice-water (100 ml.). The aqueous layer was separated from the organic layer and extracted with CHCl$_3$ (2×50 ml.). The extracts were combined with the organic layer and dried on MgSO$_4$. The solvent was removed and the oily residue was distilled in vacuo to afford 14.9g. (92%) of o-(N-methylaminomethyl)phenylacetic acid δ-lactam, boiling at 130°-135° C./2 mmHg., m.p. 35°-37° C.

ir: $\nu_{max}^{KBr}$ 3300, 1620, 1490 cm$^{-1}$.

nmr: $\delta_{ppm}^{CDCl_3}$ 3.12 (3H, s), 3.59 (2H, t, J=1.5 Hz), 4.48 (2H, t, J=1.5 Hz), 7.21 (4H, br-s).

Anal. Calc'd. for C$_{10}$H$_{11}$NO.$\frac{1}{4}$H$_2$O: C, 72.49; H, 6.84; N, 8.45. Found: C, 72.78, 72.70; H, 6.76, 6.81; N, 8.49, 8.51.

o-N-Methylaminomethylphenylacetic acid

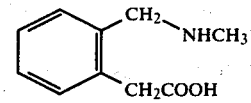

A mixture of the above-produced o-(N-methylaminomethyl)phenylacetic acid δ-lactam (5.0 g., 0.031 mol) and conc hydrochloric acid (500 ml.) was refluxed for 40 hours. The mixture as evaporated under reduced pressure, and the residual oil was dissolved in water (20 ml.) and treated with a small amount of active carbon. The filtrate was washed with benzene (50 ml.) and evaporated to dryness. The residual oil was crystallized by trituration with THF (or acetone) to give colorless needles of o-N-methylaminomethylphenylacetic acid hydrochloride (4.5 g., 67%). Anal. Calc'd. for C$_{10}$H$_{13}$NO$_2$.HCl: C, 55.69; H, 6.54; N, b 6.49; Cl, 16.44. Found: C, 55.65, 55.74; H, 6.62, 6.60; N, 6.53, 6.53; Cl, 16.36.

Some unreacted starting material was recovered from the benzene layer and the THF washings (1.2 g., 24%, b.p. 140°-143° C./2 mmHg).

An aqueous solution of o-N-methylaminomethylphenylacetic acid hydrochloride (5 g.) was column chromatographed with IR-120 ion-exchange resin (H$^+$, 70 ml.) and eluted with 3 N NH$_4$OH (2 l) to afford 3.9 g. (93%) of o-N-methylaminomethylphenylacetic acid as needles.

ir: $\nu_{max}^{KBr}$ 1650, 1470 cm$^{-1}$.

The following examples are given in illustration of, but not in limitation of, the present invention. All temperatures are in degrees Centigrade. 7-Aminocephalosporanic acid is abbreviated as 7-ACA; -ACA- represents the moiety having the structure

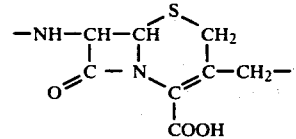

and thus 7-ACA can be represented as

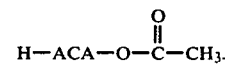

Methyl isobutyl ketone is represented as MIBK. "Skellysolve B" is a petroleum ether fraction of B.P. 60°-68° C. consisting essentially of n-hexane.

LA-1 resin is a mixture of secondary amines wherein each secondary amine has the formula

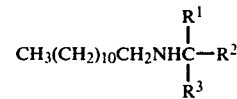

wherein each of R$^1$, R$^2$ and R$^3$ is a monovalent aliphatic hydrocarbon radical and wherein R$^1$, R$^2$ and R$^3$ contain in the aggregate from eleven to fourteen carbon atoms. This particular mixture of secondary amines, which is sometimes referred to in these examples as "Liquid Amine Mixture No. II," is a clear amber liquid having the following physical characteristics: viscosity at 25° C. of 70 cpd., specific gravity at 20° C. of 0.826; refractive index at 25° C. of 1.4554; distillation range at 10 mm., up to 170° C.—0.5%. 170°–220° C.—3%, 220°–230° C.—90% and above 230° C.—6.5%.

IR-120 is also called Amberlite IR-120 and is a strong cation exchange resin containing sulfonic acid radicals. Amberlite IR-120 is a commercially available cation exchange resin of the polystyrene sulfonic acid type; it is thus a nuclear sulfonated polystyrene resin cross-lined with divinyl benzene obtained by the procedure given by Kunin, Ion Exchange Resins, 2nd. Edition (1958), John Wiley and Sons, Inc. Therein see pages 84 and 87 for example.

Amberlite IRC-50 is a commercially available cation exchange resin of the carboxylic type; it is a copolymer of methacrylic acid and divinylbenzene.

Dicyclohexylcarbodiimide is abbreviated as DCC, tetrahydrofuran as THF, thin layer chromatography as TLC, p-toluenesulfonyl as Ts and methanol as MeOH.

When the following instrumental readings are given, for infrared nu if used is written $\nu$, for ultraviolet lambda is written as $\lambda$, with molar absorptivity as epsilon ($\epsilon$) and for nuclear magnetic resonance (nmr) delta is written as $\delta$ and tau as $\tau$ ($\delta = 10 - \tau$).

DESCRIPTION OF THE PREFERRED EMBODIMENTS

Synthesis (Schemes 1, 2 and 3)

The 3-side chain thiol, 2-carboxymethyl-2,3-dihydro-s-triazolo[4,3-b]pyridazin-3-on-6-ylthiol (3), was prepared by N-ethoxycarbonylmethylation of 6-chloro-2,3-dihydro-s-triazolo[4,3-b]pyridazin-3-one (1) with sodium hydride and ethyl chloroacetate in DMF (dimethylformamide) and subsequent thiolation with sodium hydrosulfide (Scheme 1). Condensation of 7-ACA (7-aminocephalosporanic acid) with 3 carried out by refluxing in phosphate buffer (pH 7) to give the 3-substituted-thio 7-ACA (4), which was coupled with an appropriate N-BOC-protected amino acid by the active ester method using 2,4-dinitrophenol (DNP). The resulting N-BOC-protected cephalosporins 7 and 11 were deblocked with TFA (trifluoroacetic acid) and converted to the monosodium salt with N sodium hydroxide (Schemes 2 and 3).

Scheme 1. Preparation of 7-Amino-3-(2-carboxymethyl-2,3-dihydro-s-triazolo[4,3-b]pyridazin-3-on-6-ylthiomethyl)-3-cephem-4-carboxylic Acid

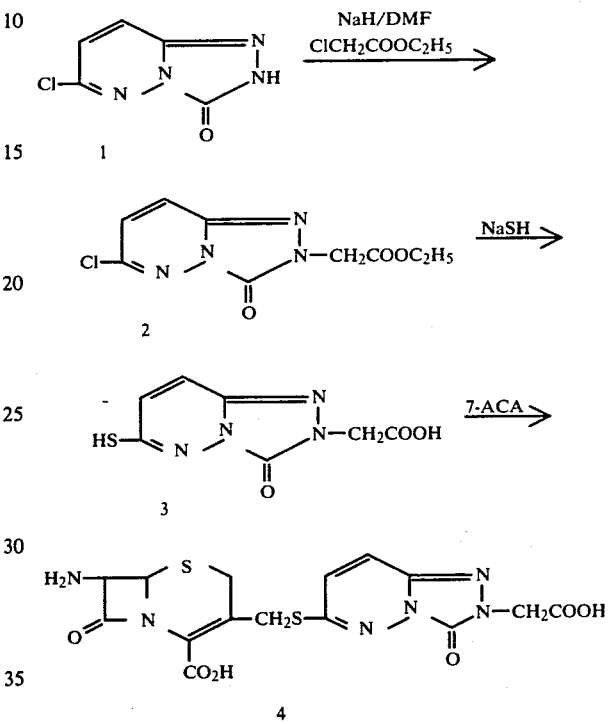

Scheme 2. Preparation of 7-[(o-Aminomethylphenyl)acetamido]-3-(2-carboxymethyl-2,3-dihydro-s-triazolo[4,3-b]pyridazin-3-on-6-ylthiomethyl)-3-cephem-4-carboxylic Acids

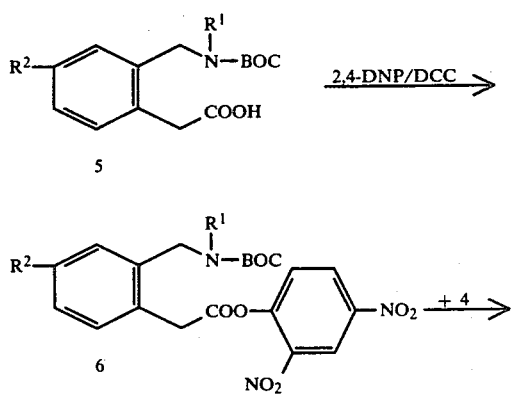

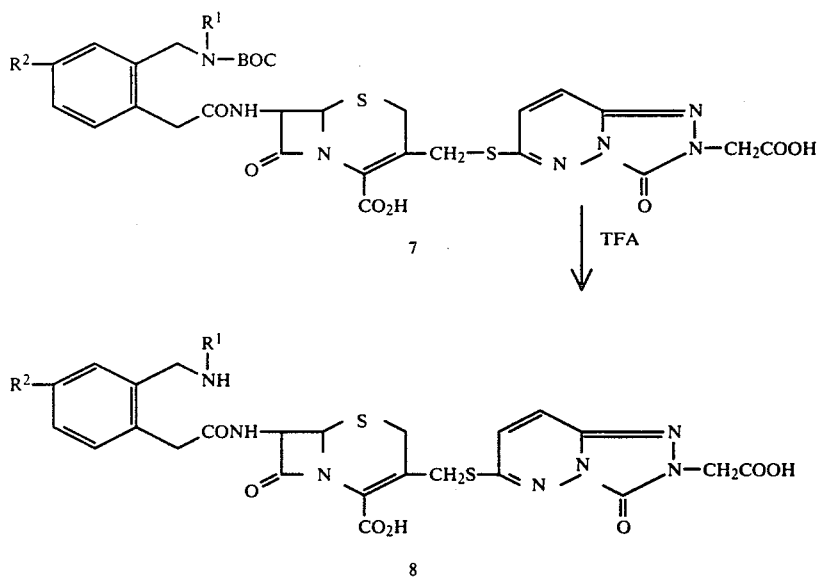
a: $R^1$ = H, $R^2$ = H
b: $R^1$ = $CH_3$, $R^2$ = H
c: $R^1$ = $CH_3$, $R^2$ = OH
8a: BB-S469
8b: BB-S479
8c: BB-S478
Scheme 3. Preparation of
7-(3-Aminomethyl-2-thienylacetamido)-3-(2-carboxymethyl-2,3-dihydro-s-triazolo[4,3-b]pyridazin-3-on-6-ylthiomethyl)-3-cephem-4-carboxylic Acids
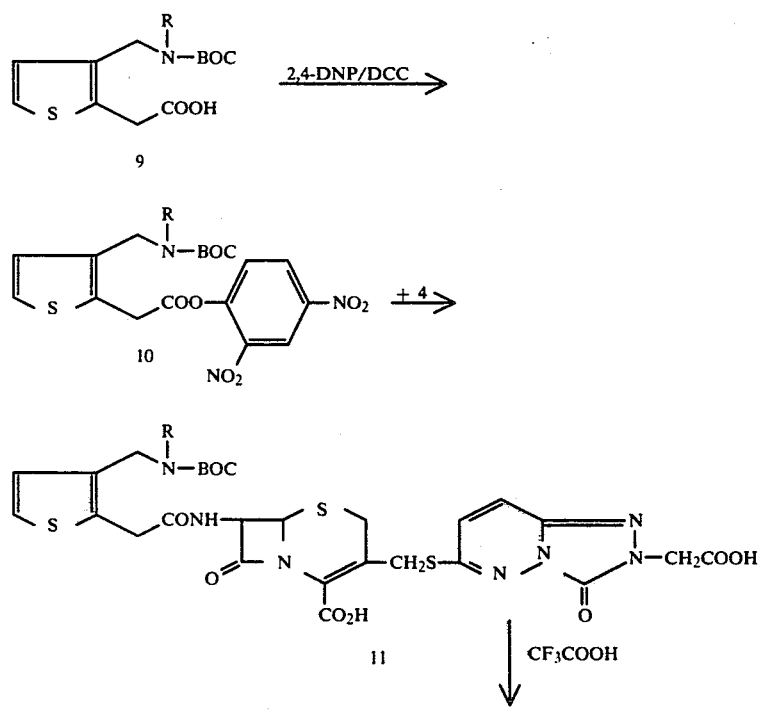

-continued

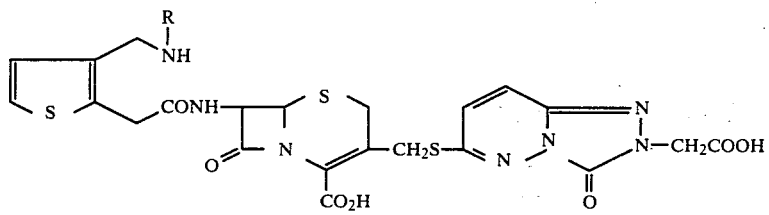

a: R = H
b: R = CH₃
12a: BB-S483
12b: BB-S472

6-Chloro-2,3-dihydro-2-ethoxycarbonylmethyl-s-triazolo[4,3-b]pyridazin-3-one (2)

To a solution of 6-chloro-2,3-dihydro-s-triazolo[4,3-b]pyridazin-3-one [P. Francavilla and F. Lauria, J. Het. Chem., 8, 415 (1971)] (1, 1.00 g., 5.9 m.mole) in dry DMF (30 ml.) was added sodium hydride (50% in paraffin, 0.3 g., 6.3 m.mole) under stirring with formation of yellow crystals. To the mixture was added ethyl chloroacetate (1.4 ml., 13 m.mole) and the mixture was heated at 90° C. for 8 hours with stirring. After cooling, the reaction mixture was poured into water (50 ml.) and extracted with toluene (5×40 ml.). The organic extracts were combined, dried over anhydrous sodium sulfate and evaporated at reduced pressure. The residue was crystallized with benzene-n-hexane to give yellow needles of 2 (1.16 g., 77%), m.p. 114°–115° C. (lit. 110° C.).
ir: $\nu_{max}^{KBr}$ 1735, 1710 cm$^{-1}$.
uv: $\lambda_{max}^{EtOH}$ 231 nm ($\epsilon$, 26000)
nmr: $\delta_{ppm}^{CDCl_3}$ 7.58 (1H, d, J=10 Hz, pyridazine-H), 6.98 (1H d, J=10 Hz, pyridazine-H), 4.80 (2H, s, -CH₂CO), 4.27 (2H, q, J=7.5 Hz, CH₂CH₃), 1.29 (3H, t, J=7.5 Hz, CH₂CH₃).
Anal. Calc'd. for C₉H₉N₄O₃Cl: C, 42.12; H, 3.53; N, 21,83; Cl, 13.81. Found: C, 41.54, 41.46; H, 3.22, 3.49; N, 21.51, 21.53; Cl, 13.88, 13.99.

2-Carboxymethyl-2,3-dihydro-6-mercapto-s-triazolo[4,3-b]pyridazin-3-one (3)

To a solution of 6-chloro-2,3-dihydro-2-ethoxycarbonylmethyl-s-triazolo[4,3-b]pyridazin-3-one (2, 30 g., 0.12 mole) in ethanol (900 ml.) was added NaSH.2H₂O (70% pure, 45.9 g., 0.36 mole) and the mixture was refluxed for 0.5 hour. The reaction mixture was evaporated at reduced pressure. The residue was dissolved in water (200 ml.) and concentrated HCl was added to the solution to adjust to pH 2. The precipitate (3) was collected by filtration and washed with water. Yield 18.3 g. (69%).
ir: $\nu_{max}^{KBr}$ 2900, 2450, 1750, 1660 cm$^{-1}$.
uv: $\lambda_{max}^{1\%NaHCO_3aq.}$ 260 nm ($\epsilon$, 19500), 313 nm ($\epsilon$, 7000)

nmr: $\delta_{ppm}^{DMSO-d_6}$ 7.88 (1H, d, J=10 Hz, pyridazine-H), 7.45 (1H, d, J=10 Hz, pyridazine-H), 4.72 (2H, s, CH₂CO).
Anal. Calc'd. for C₇H₆N₄O₃S: C, 37.17; H, 2.67; N, 24.77; S, 14.17. Found: C, 37.35, 37.23; H, 2.26, 2.28; N, 23.58, 23.69; S, 14.32.

7-Amino-3-(2-carboxymethyl-2,3-dihydro-s-triazolo[4,3-b]pyridazin-3-on-6-ylthiomethyl)-3-cephem-4-carboxylic Acid (4)

To a suspension of 7-aminocephalosporanic acid (8.79 g., 32.2 m.mole) in 0.1 M phosphate buffer (pH 7, 149 ml.) were added NaHCO₃ (8.14 g., 97.0 m.mole) and the thiol 3 (7.30 g., 32.2 m.mole) with stirring. The mixture was heated at 80° C. for 0.5 hour under N₂ stream. The mixture was treated with active carbon and adjusted to pH 3 with concentrated HCl. The resulting precipitate was collected by filtration and washed with water to give 7.59 g. (54%) of 4.
ir: $\nu_{max}^{KBr}$ 1800, 1720, 1600, 1540, 1470 cm$^{-1}$.
uv: $\lambda_{max}^{Buffer (pH 7)}$ 252 nm ($\epsilon$, 19500), 298 nm ($\epsilon$, 8400).
nmr: $\delta_{ppm}^{D_2O+K_2CO_3}$ 7.56 (1H, d, J=9 Hz, pyridazine-H), 7.05 (1H, d, J=9 Hz, pyridazine-H), 5.45 (1H, d, J=5 Hz, 6-H), 5.05 (1H, d, 5 Hz, 7-H), 4.43 (1H, d, J=14 Hz, 3-CH₂), 4.04 (1H, d, J=14 Hz, 3-CH₂), 3.88 (1H, d, J=18 Hz, 2-H), 3.45 (1H, d, J=18 Hz, 2-H).

EXAMPLE 1

Preparation of BB-S469

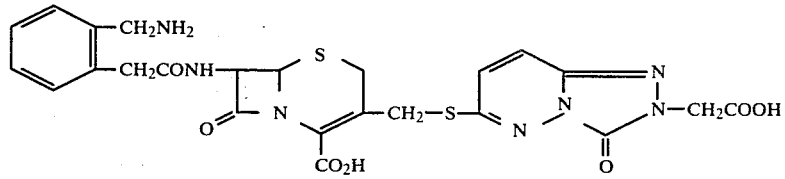

8a, BB-S469

2,4-Dinitrophenyl o-(N-butoxycarbonylaminomethyl)phenylacetate (6a)

To a mixture of o-(N-butoxycarbonylaminomethyl)-phenylacetic acid (5a, 13 g., 49 m.mole) and 2,4-dinitrophenol (9.02 g., 49 m.mole) in dry ethyl acetate (123 ml.) was added dicyclohexylcarbodiimide (DCC) (10.1 g., 49 m.mole) under water cooling (5°–15° C.), and the mixture was stirred for 30 minutes at the same temperature and then for 40 minutes at room temperature. The resulting precipitate was filtered off and the filtrate was evaporated to give 23.9 g. of the active ester 6a, which was used in the next acylation reaction without further purification.

ir: $\nu_{max}^{KBr}$ 1775, 1700, 1600, 1530 cm$^{-1}$.

7-[o-(N-Butoxycarbonylaminomethyl)-phenylacetamido]-3-(2-carboxymethyl-2,3-dihydro-s-triazolo[4,3-b]pyridazin-3-on-6-ylthiomethyl)-3-cephem-4-carboxylic Acid (7a)

To a cold (0° C.) mixture of 4 (4.38 g., 10 m.mole), Et$_3$N (4.5 ml., 30 m.mole), CH$_3$CN (20 ml.) and water (20 ml.) was added a solution of 2,4-dinitrophenyl o-(N-butoxycarbonylaminomethyl)phenylacetate (6a, 4.79 g.) in THF (tetrahydrofuran) (20 ml.). After stirring at room temperature overnight, THF and CH$_3$CN in the reaction mixture were removed at reduced pressure and the resulting aqueous solution was adjusted to pH 2 with dilute HCl and extracted with ethyl acetate (10×30 ml.). The organic extracts were dried over sodium sulfate and evaporated. The residue was chromatographed on a column of silica gel (60 g.) and eluted with CHCl$_3$ and 3% MeOH-CHCl$_3$ successively to give 2.40 g. (37%) of 7a, mp. >161° C. (dec.).

ir: $\nu_{max}^{KBr}$ 1780, 1720 cm$^{-1}$.
uv: $\lambda_{max}^{pH\ 7\ Buffer}$ 252 nm ($\epsilon$, 19800), 298 nm ($\epsilon$, 8900).
nmr: $\delta_{ppm}^{DMSO+D2O}$ 7.67 (1H, d, J=9.0 Hz, pyridazine-H), 7.10 (4H, s, phenyl-H), 7.05 (1H, d, J=9.0 Hz, pyridazine-H), 5.66 (1H, d, J=4.5 Hz, 7-H), 5.07 (1H, d, J=4.5 Hz, 6-H), 4.71 (2H, s, N-CH$_2$-CO), 4.4–4.0 (4H, m, 3-CH$_2$ & CH$_2$-N), 3.8–3.5 (4H, m, 2-H & CH$_2$CO), 1.42 (9H, s, t-Butyl-H).

Anal. Calc'd. for C$_{28}$H$_{31}$N$_7$O$_7$S$_2$.2H$_2$O: C, 49.62; H, 5.20; N, 14.46; S, 9.46. Found: C, 49.97, 49.95; H, 4.79, 4.62; N, 14.00, 13.84; S, 9.37, 9.32.

BB-S469; 7-[(o-(Aminomethylphenyl)acetamido]-3-(2-carboxymethyl-2,3-dihydro-s-triazolo[4,3-b]pyridazin-3-on-6-ylthiomethyl)-3-cephem-4-carboxylic Acid (8a)

Trifluoroacetic acid (3.4 ml.) was added to 7a (2.33 g.) at 0° C. and the mixture stirred for 15 minutes at room temperature. To the mixture was added dry ether (100 ml.), and the precipitate was collected by filtration and washed with dry ether (2×50 ml.). The solid was dissolved in a mixture of CH$_3$CN (100 ml.) and water (14 ml.) and the solution was adjusted to pH 4–5 with concentrated NH$_4$OH to afford a precipitate which was collected by filtration and washed with CH$_3$CN (2×50 ml.) to give 1.75 g. (82%) of 8a as the ammonium salt. M.p. >160° C. (dec.).

ir: $\nu_{max}^{KBr}$ 1765, 1710, 1640, 1590 cm$^{-1}$.
uv: $\lambda_{max}^{pH\ 7\ Buffer}$ 252 nm ($\epsilon$, 23900), 298 nm ($\epsilon$, 10900).
Anal. Calc'd. for C$_{24}$H$_{22}$N$_7$O$_7$S$_2$.NH$_4^+$.H$_2$O: C, 46.51; H, 3.96; N, 18.08; S, 10.35. Found: C, 46.52, 46.26; H, 4.15, 4.19; N, 17.60, 17.48; S, 10.89, 10.41.

Preparation of BB-S469 Monosodium Salt

To a suspension of 8a (1.58 g.) in 50% acetone-water (30 ml.) was added a 10% solution to adjust the pH to 7.7. An additional amount of acetone was added and the precipitate was collected by filtration and washed with acetone to give 1.38 g. (87%) of monosodium salt of 8a, m.p. >170° C. (dec.).

ir: $\nu_{max}^{KBr}$ 1765, 1710, 1640, 1600, 1540, 1485 cm$^{-1}$.
uv: $\lambda_{max}^{pH\ 7\ Buffer}$ 252 nm ($\epsilon$, 20600), 298 nm ($\epsilon$, 9200).
nmr: $\delta_{ppm}^{D2O+K2CO3}$ 7.52 (1H, d, J=9 Hz, pyridazine-H), 7.27 (4H, s, phenyl-H), 7.03 (1H, d, J=9 Hz, pyridazine-H), 5.62 (1H, d, J=4.5 Hz, 7-H), 5.07 (1H, d, J=4.5 Hz, 6-H).

Anal. Calc'd. for C$_{24}$H$_{22}$N$_7$O$_7$S$_2$Na.2H$_2$O: C, 44.79; H, 4.07; N, 15.23; S, 9.96. Found: C, 44.44, 44.95; h, 3.68, 3.90; N, 16.50, 16.67; S, 10.38, 10.45.

EXAMPLE 2

Preparation of BB-S472

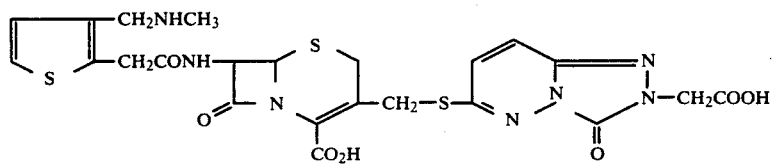

12b, BB-S472

7-(3-N-t-Butoxycarbonyl-N-methylaminomethyl-2-thienylacetamido)-3-(2-carboxymethyl-2,3-dihydro-s-triazolo[4,3-b]pyridazin-3-on-6-ylthiomethyl)-3-cephem-4-carboxylic Acid. (11b)

A mixture of the BOC-protected amino acid (10b, 513 mg., 1.8 m.mole), 2.4-dinitrophenol (400 mg., 2.16 m.mole) and DCC (445 mg., 2.16 m.mole) in THF (5 ml.) was stirred at room temperature for 12 hours. The precipitated urea was removed and the filtrate was added to a mixture of 7-amino-3-(2-carboxymethyl-2,3-dihydro-s-triazolo[4,3-b]pyridazin-3-on-6-ylthiomethyl)-3-cephem-4-carboxylic acid (4, 800 mg., 1.8 m.mole) and triethylamine (0.76 ml., 5.4 m.mole) in water (5 ml.) at 0° C. with stirring. Stirring was continued until active ester had disappeared on tlc (silica gel plate; Rf 0.95; solvent system, CHCl$_3$:MeOH=3:1). The reaction mixture was diluted with water (20 ml.), layered with AcOEt (50 ml.) and adjusted to pH 2 with concentrated HCl at 5° C. The organic layer was separated and aqueous layer was extracted with AcOEt (3×50 ml.). The AcOEt extracts were combined, washed with sat. aq. NaCl, dried over MgSO$_4$ and concentrated under reduced pressure. The residual oil (1.9 g.) was chromatographed on silica gel (40 g.). The column was eluted successively with CHCl$_3$ (400 ml.), 3% MeOH-CHCl$_3$ (100 ml.) and 10% MeOH-CHCl$_3$ while monitoring with tlc (silica gel plate, solvent system MeOH:CHCl$_3$=1:2, detected with I$_2$). From the CHCl$_3$ eluate was recovered a mixture of 2,4-DNP and the BOC-protected amino acid 9 and 3% MeOH-CHCl$_3$ eluate 50 mg. of 9. The desired product (11b) (Rf 0.4, solvent system CHCl$_3$:MeOH=3:1) was obtained by evaporation of the eluate with 10% MeOH—CHCl$_3$. Yield 490 mg. (39%). M.p. 215°–220° C.

ir: $\nu_{max}^{KBr}$ 3400, 1780, 1720, 1680, 1550 cm$^{-1}$.
uv: $\lambda_{max}^{pH\ 7\ Buffer}$ 245 nm ($\epsilon$, 23000), 260 nm ($\epsilon$, 18000), 300 nm ($\epsilon$, 7900).
nmr: $\delta_{ppm}^{DMSO-d6}$ 1.42 (9H, s, BOC—H), 2.75 (3H, s, N—CH$_3$), 3.80

(4H, br-s, 2-H & S—C(H)(H)—CO), 4.35 (4H, br-s, H₂C—N & 3-CH₂), S  5

4.72 (2H, s, BOC-N-CH₂), 5.10 (1H, d, J=4.5 Hz, 6-H), 5.70 (1H, d-d, J=4.5 & 10.5 Hz, changed to a doublet J=4.5 by addition of D₂O, 7-H), 6.85 (1H, d, J=4.5 Hz, thiophene Hβ), 7.19 (1H, d, J=9 Hz, pyridazine H), 7.34 (1H, d, J=4.5 thiophene Hα), 7.72 (1H, d, J=9 Hz, pyridazine-H), 9.11 (1H, d, J=10.5 Hz, disappeared by addition of D₂O, NH).

Anal. Calc'd. for $C_{28}H_{31}N_7O_9S_3 \cdot H_2O$: C, 46.46; H, 4.60; N, 13.55; S, 13.29. Found: C, 46.67; H, 4.71; N, 12.79; S, 12.81.

BB-S472;

7-(3-Methylaminomethyl-2-thienylacetamido)-3-(2-carboxymethyl-2,3-dihydro-s-triazolo[4,3-b]pyridazin-3-on-6-ylthiomethyl)-3-cephem-4-carboxylic Acid (12b)

Trifluoroacetic acid (0.4 ml.) was added to 11b (400 mg., 0.57 m.mole) at 0° C. and the mixture was stirred at room temperature for 15 minutes. To the reaction mixture was added anhydrous ether (10 ml.) to separate a precipitate which was collected by filtration, washed with anhydrous ether (2×10 ml.) and suspended in acetonitrile (10 ml.). The suspension was adjusted to pH 4 with concentrated NH₄OH and stirred for 10 minutes. The solid was collected by filtration, washed with acetonitrile (2×5 ml.) and dried at 60° C./1 mmHg for 7 hours to afford 310 mg. (90%) of 12b melting at 188°–191° C. (dec.).

ir: $\nu_{max}^{KBr}$ 3400, 1770, 1720, 1680, 1550 cm⁻¹.

uv: $\lambda_{max}^{pH\ 7\ Buffer}$ 245 nm (ε, 22400), 260 nm (ε, 18700), 300 nm (ε, 8600).

Anal. Calc'd. for $C_{23}H_{23}N_7O_7S_3 \cdot 3H_2O$: C, 41.87; H, 4.43; N, 14.86; S, 14.58. Found: C, 42.03; H, 3.59; N, 14.79; S, 14.35.

Preparation of BB-S472 Monosodium Salt

To a suspension of 12b (230 mg., 0.38 m.mole) in 0.5 ml. of deionized water was added N NaOH to adjust to pH 8.9. Acetone (15 ml.) was added to the solution. The precipitate was collected by filtration, washed with acetone (2×50 ml), and dried at 60° C./1 mmHg for 7 hours to afford 170 mg. (71%) of monosodium salt of BB-S472, m.p. ≦210° C. (dec.).

ir: $\nu_{max}^{KBr}$ 3400, 1765, 1710, 1680, 1600 cm⁻¹.

uv: $\lambda_{max}^{pH\ 7\ Buffer}$ 245 nm (ε, 21800), 260 nm (ε, 18500), 300 nm (ε, 7800).

nmr: $\delta_{ppm}^{D_2O}$ 2.72 (3H, s, N—CH₃), 3.45 (1H, d, J=18 Hz, 2—H), 3.75 (1H, d, J=18 Hz, 2—H), 3.95

(2H, s, S—C(=O)—CH₂CO), 4.18 (4H, m, —CH₂N & 3-CH₂), S 4.57 (2H, s, N—CH₂), 5.00 (1H, d, J=4.5 Hz, 6—H), 5.53 (1H, d, J=4.5 Hz, 7—H), 6.97 (1H, d, J=9 Hz, pyridazine—H), 7.03 (1H, d, J=4.5 Hz, thiophene—Hβ), 7.34 (1H, d, J=4.5 Hz, thiophene—Hα), 7.48 (1H, d, J=9 Hz, pyridazine—H).

Anal. Calc'd. for $C_{23}H_{22}N_7O_7S_3Na \cdot 1/2H_2O$: C, 43.40; H, 3.64; N, 15.40; S, 15.11. Found: C, 43.26; H, 4.08; N, 14.18; S, 13.91.

EXAMPLE 3

Preparation of BB-S478

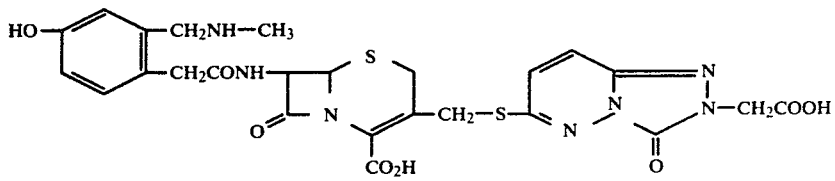

8c, BB-S478

7-[2-(N-t-Butoxycarbonyl-N-methylaminomethyl)-4-hydroxyphenylacetamido]-3-(2-carboxymethyl-2,3-dihydro-s-triazolo-[4,5-b]pyridazin-3-on-6-ylthiomethyl)-3-cephem-4-carboxylic Acid (7c)

A mixture of 2-N-t-butoxycarbonyl-N-methylaminomethyl-4-hydroxyphenylacetic acid (5c), (708 mg., 2.4 m.mole), 2,4-dinitrophenol (478 mg., 2.6 m.mole) and DCC (536 mg., 2.6 m.mole) in dry THF (20 ml.) was stirred at room temperature for 2 hours. The precipitated urea was removed by filtration. The filtrate was added to a solution of 7-amino-3-(2-carboxymethyl-2,3-dihydro-s-triazolo[4,5-b]pyridazin-3-on-6-ylthiomethyl)-3-cephem-4-carboxylic acid (4) (876 mg., 2 m.mole) in 20 ml. of water containing triethylamine (0.84 ml., 6 m.mole) and the mixture was stirred at room temperature for 18 hours. After concentrating to 20 ml. the aqueous solution was washed with ether, acidified with 6N HCl and extracted with 200 ml. of ethyl acetate. The extract was filtered to remove insolubles, washed with water and a saturated aqueous NaCl solution and dried. The solution was evaporated to dryness and the oily residue was chromatographed on a silica gel (Wakogel C-200, 25 g.) eluting with chloroform and 3% of chloroform-methanol. The fractions containing the desired product (monitored by tlc; Rf 0.3; solvent system, CHCl₃:MeOH=2:1) were collected and evaporated to dryness. The oily residue was triturated with ether-n-hexane to give 630 mg. (44%) of the product 7c melting at 200°–210° C. (slow dec.).

ir: $\nu_{max}^{KBr}$ 1780, 1720, 1660, 1400, 1240, 1150 cm⁻¹.

uv: $\lambda_{max}^{pH\ 7\ Buffer}$ 252 nm (ε, 13000), 300 nm (ε, 5400).

nmr: $\delta_{ppm}^{DMSO-d_6}$ 1.39 (9H, s, C—CH₃), 2.73 (3H, s, N—CH₃), 3.3–3.9 (4H, m, CH₂CO & 2—H), 4.35 (4H, m, CH₂N & 3—H), 4.48 (2H, s, NCH₂CO), 5.03 (1H, d, 4.5 Hz, 6—H), 5.61 (1H, d-d, 8 & 4.5 Hz, 7—H), 6.4–7.2 (3H, m, phenyl—H), 6.98 (1H, d, 10 Hz, pyridazine—H), 7.61 (1H, d, 10 Hz, pyridazine—H), 8.87 (1H, d, 8 Hz, NH).

Anal. Calc'd for $C_{30}H_{33}N_7O_{10}S_2$: C, 50.34; H, 4.65; N, 13.70; S, 8.96. Found: C, 50.98; H, 5.36; N, 11.88; S, 7.60.

BB-S478;
7-(2-N-Methylaminomethyl-4-hydroxyphenylacetamido)-3-(2-N-carboxymethyl-2,3-dihydro-s-triazolo[4,5-b]pyridazin-3-on-6-ylthiomethyl)-3-cephem-4-carboxylic Acid (8c)

A mixture of 7c (570 mg., 0.8 m.mole) and trifluoroacetic acid (1.5 ml.) was stirred at 10° C. for 30 minutes and the mixture was diluted with ether (50 ml.) to separate the trifluoroacetate of 8c which was collected by filtration and then dissolved in a mixture of 10 ml. of acetonitrile and 5 ml. of water and then filtered. The filtrate was adjusted to pH 6 with concentrated ammonium hydroxide and the mixture was diluted with acetonitrile (100 ml.). The resulting precipitate was collected by filtration, washed with acetonitrile and dried in vacuo over $P_2O_5$ to give 370 mg. (75%) of 8c, melting at 215°-220° C. (dec.).

ir: $\nu_{max}^{KBr}$ 1770, 1710, 1600, 1380, 1350 $cm^{-1}$.
uv: $\lambda_{max}^{pH\ 7\ Buffer}$ 252 nm ($\epsilon$, 19000), 300 nm ($\epsilon$, 9100).
nmr: $\delta_{ppm}^{D_2O+K_2CO_3}$ 2.75 (3H, s, N—CH$_3$), 2.9–3.3 (4H, m, $\underline{CH_2}$CO & 2—H), 4.0–4.3 (4H, m, CH$_2$N & 3—H), 4.57 (2H, s, NCH$_2$CO), 4.81 (1H, d, 4.5 Hz, 6—H), 5.53 (1H, d, 4.5 Hz, 7—H), 6.6–7.5 (5H, m, phenyl—H & pyridazin—H).

Anal. Calc'd. for $C_{25}H_{25}N_7O_8S_2.5/2H_2O$: C, 45.45; H, 4.58; N, 14.84; S, 9.71. Found: C, 45.69; H, 4.21; N, 15.03; S, 9.46.

Preparation of Monosodium Salt of BB-S478

To a suspension of 8c (308 mg., 0.5 m.mole) in water (2 ml.) was added 0.3–0.4 ml. of N NaOH and the mixture was stirred at room temperature; the pH of the resulting solution was 9.2. Acetone (20 ml.) was slowly added to the solution. The resulting precipitate was collected by filtration, washed with acetone (10 ml.) and dried in vacuo over $P_2O_5$ to give 290 mg. (91%) of the monosodium salt of BB-S478, melting at 230°–235° C. (dec.).

ir: $\nu_{max}^{KBr}$ 1770, 1700, 1600, 1390, 1350 $cm^{-1}$.
uv: $\lambda_{max}^{pH\ 7\ Buffer}$ 250 nm ($\epsilon$, 18000), 300 nm ($\epsilon$, 8400).

Anal. Calc'd. for $C_{25}H_{24}N_7O_8S_2Na.5/2H_2O$: C, 43.98; H, 4.28; N, 14.36; S, 9.39. Found: C, 43.96; H, 4.14; N, 13.51; S, 9.34.

EXAMPLE 4
Preparation of BB-S479

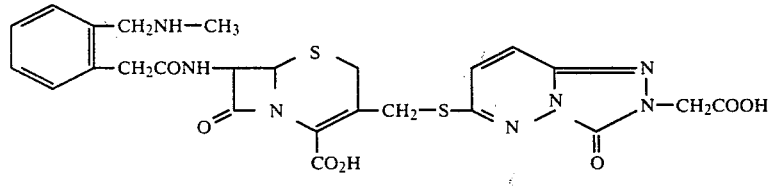

8b, BB-S479

7-[o-(N-Butoxycarbonyl-N-methylaminomethyl)-phenylacetamido]-3-(2-carboxymethyl-2,3-dihydro-s-triazolo[4,3-b]pyridazin-3-on-6-ylthiomethyl)-3-cephem-4-carboxylic Acid (7b)

To a cold (0° C.) mixture of 4 (5.4 g., 12 m.mole), Et$_3$N (5.5 ml.), CH$_3$CN (25 ml.) and water (25 ml.) was added a solution of 2,4-dinitrophenyl o-(N-butoxycarbonyl-N-methylaminomethyl)phenylacetate (6b) in THF [prepared from o-(N-butoxycarbonyl-N-methylaminomethyl)phenylacetic acid (5b) (3.48 g., 13.5 m.mole), 2,4-dinitrophenol (2.49 g., 13.5 m.mole) and DCC (2.79 g., 13.5 m.mole) in dry THF (37 ml.)]. The mixture was stirred at room temperature overnight. THF and CH$_3$CN were removed from the reaction mixture by evaporation under reduced pressure and the resulting aqueous solution was washed with ether (3×30 ml.), adjusted to pH 2–3 with dilute HCl and extracted with ethyl acetate (4×30 ml). The organic extracts were combined, dried over sodium sulfate and evaporated. The residue was chromatographed on a column of SiO$_2$ (100 g.). After washing with CHCl$_3$, the column was eluted with 3% MeOH in CHCl$_3$ to afford a desired fraction containing 7b. Yield 3.8 g. (45%). m.p.>200° C. (dec.).

ir: $\nu_{max}^{KBr}$ 1780, 1720, 1680 $cm^{-1}$.
uv: $\lambda_{max}^{pH\ 7\ Buffer}$ 250 nm ($\epsilon$, 18800), 297 nm ($\epsilon$, 8400).
nmr: $\delta_{ppm}^{DMSO+D_2O}$ 7.62 (1H, d, J=10.5 Hz, pyridazine—H), 7.14 (4H, s, phenyl—H), 6.98 (1H, d, J=10.5 Hz, pyridazine—H), 5.61 (1H, d, J=4.5 Hz, 7—H), 5.03 (1H, d, J=4.5 Hz, 6—H), 4.67 (2H, s, N—CH$_2$), 4.42 (2H, s, CH$_2$—N), 4.4–4.0 (2H, m, 3—CH$_2$), 3.8–3.4 (4H, m, 2—H & CH$_2$—CO), 2.72 (3H, s, N—CH$_3$), 1.38 (9H, s, BOC—H).

Anal. Calc'd for $C_{30}H_{33}N_7O_9S_2.5/2H_2O$: C, 48.38; H, 5.14; N, 13.16; S, 8.61. Found: C, 48.25, 48.23; H, 4.52, 4.46; N, 12.93, 12.86; S, 8.68.

BB-S479;
7-[o-(Methylaminomethyl)phenylacetamido]-3-(2-carboxymethyl-2,3-dihydro-s-triazolo[4,3-b]pyridazin-3-on-6-ylthiomethyl)-3-cephem-4-carboxylic Acid (8b)

Trifluoroacetic acid (7 ml.) was added to the t-BOC-derivative 7b (3.8 g., 5.5 m.mole) at 0° C., and the mixture was stirred for 20 minutes at room temperature. Dry ether (100 ml.) was added to the mixture. The resulting precipitate was collected by filtration and washed with dry ether (3×100 ml.). The precipitate was dissolved in a mixture of CH$_3$CN (120 ml.) and water (18 ml.) and the solution was adjusted to pH 5–6 with concentrated NH$_4$OH to give an oily precipitate which was triturated with CH$_3$CN to form solid material. The product 8b was collected by filtration, washed with CH$_3$CN and dried. Yield 2.55 g. (77%).

ir: $\nu_{max}^{KBr}$ 1770, 1710, 1600, 1550 $cm^{-1}$.

Preparation of Monosodium Salt of BB-S479

To a solution of BB-S479 (8b) (2.54 g., 4.3 m.mole) in water (25 ml.), N NaOH (ca. 3 ml.) was added under cooling (the pH of the solution was 10). A large amount of acetone was added to the solution and the precipitate was collected by filtration and washed with acetone to give 1.94 g. (84%) of monosodium salt of BB-S479. M.p. >200° C. (dec.).

ir: $\nu_{max}^{KBr}$ 1770, 1710, 1600, 1550 cm$^{-1}$.
uv: $\lambda_{max}^{pH\ 7\ Buffer}$ 250 nm ($\epsilon$, 19400), 297 nm ($\epsilon$, 8700).

Anal. Calc'd for $C_{25}H_{24}N_7O_7S_2Na.1/2H_2O$: C, 47.61; H, 4.00; N, 15.55; S, 10.17. Found: C, 47.43, 47.43; H, 4.67, 4.68; N, 15.97, 15.70; S, 9.25, 9.84.

EXAMPLE 5

Preparation of BB-S482

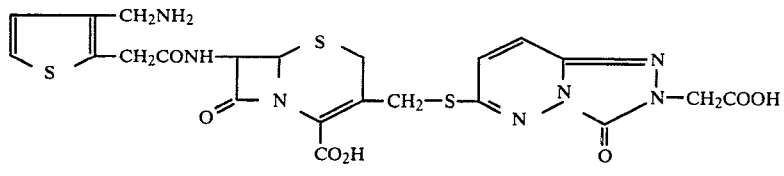

12a, BB-S483

7-(3-N-t-Butoxycarbonylaminomethyl-2-thienylacetamido)-3-(2-carboxymethyl-2,3-dihydro-s-triazolo[4,3-b]pyridazin-3-on-6-ylthiomethyl)-3-cephem-4-carboxylic Acid (11a)

A mixture of the BOC-protected amino acid (9, 410 mg., 1.56 m.mole), 2,4-dinitrophenol (313 mg., 1.7 m.mole) and DCC (353 mg., 1.7 m.mole) in THF (5 ml.) was stirred at room temperature for 12 hours. The precipitated urea was removed and the filtrate was added to a mixture of 7-amino-3-(2-carboxymethyl-2,3-dihydro-s-triazolo[4,3-b]-pyridazin-3-on-6-ylthiomethyl)-3-cephem-4-carboxylic acid (4, 683 mg., 1.56 m.mole) and triethylamine (0.62 ml., 4.68 m.mole) in water (5 ml.) at 0° C. with stirring. Stirring was continued at room temperature until the active ester disappeared on tlc (silica gel plate; Rf 0.95; solvent system, CHCl$_3$:MeOH=3:1). The reaction mixture was diluted with water (20 ml.), layered with AcOEt (50 ml.) and adjusted to pH 2 with concentrated HCl at 5° C. The organic layer was separated and the aqueous layer was extracted with AcOEt (3×50 ml.). The AcOEt (ethyl acetate) extracts were combined, washed with saturated aqueous NaCl, dried over MgSO$_4$ and concentrated under reduced pressure. The residual oil (1.8 g.) was chromatographed on silica gel (40 g.). The column was eluted successively with CHCl$_3$ (400 ml.) and 3% MeOH—CHCl$_3$ (500 ml.). The eluate was monitored with tlc (silica gel plate, solvent system CHCl$_3$:MeOH=2:1, detected with I$_2$). The desired product 11a (Rf 0.2) was obtained by evaporation of the MeOH—CHCl$_3$ eluate. Yield 450 mg. (42%), melting at 155°–160° C.

ir: $\nu_{max}^{KBr}$ 3300, 1775, 1720, 1680 cm$^{-1}$.
uv: $\lambda_{max}^{pH\ 7\ Buffer}$ 245 nm ($\epsilon$, 23900), 260 nm ($\epsilon$, 19200), 300 nm ($\epsilon$, 8700).
nmr: $\delta_{ppm}^{DMSO-d_6}$ 1.39 (9H, s, BOC-H), 3.76

(4H, br-s, 2-H & S CH$_2$CO), 4.05 (2H, d, J=6 Hz, changed to a singlet by addition of D$_2$O, BOCNH—C$\underline{H}_2$), 4.20 (2H, m, 3-CH$_2$), 4.69 (2H, s, N—CH$_2$CO$_2$), 5.06 (1H, d, J=4.5 Hz, 6—H), 5.62 (1H, d-d, J=4.5 & 9 Hz, changed to a doublet J=4.5 Hz by addition of D$_2$O, 7—H), 6.83 (1H, d, J=4.5 Hz, thiophene—H$\beta$), 7.00 (1H, m, disappeared by addition of D$_2$O, N$\underline{H}$BOC), 7.04 (1H, d, J=9 Hz, pyridazine—H), 7.12 (1H, d, J=4.5 Hz, thiophene- H$\alpha$), 7.65 (1H, d, J=9 Hz, pyridazine-H), 8.97 (1H, d, J=9 Hz, disappeared by addition of D$_2$O, 7—NH).

Anal. Calc'd. for $C_{27}H_{29}N_7O_9S_3$: C, 46.88; H, 4.23; N, 14.17; S, 13.90. Found: C, 46.42; H, 4.37; N, 13.49; S, 13.61.

BB-S 483;
7-(3-Aminomethyl-2-thienylacetamido)-3-(2-carboxymethyl-2,3-dihydro-s-triazolo[4,3-b]pyridazin-3-on-6-ylthiomethyl)-3-cephem-4-carboxylic Acid (12a)

Trifluoroacetic acid (0.4 ml.) was added to 11a (410 mg., 0.59 m.mole) at 0° C. and the mixture was stirred at room temperature for 15 minutes. To the reaction mixture was added anhydrous ether (10 ml.) to separate a precipitate which was collected by filtration, washed with anhydrous ether (2×10 ml.) and suspended in acetonitrile (10 ml). The suspension was adjusted to pH 4 with concentrated NH$_4$OH and stirred for 10 minutes. The precipitate was collected by filtration, washed with acetonitrile (2×5 ml.) and dried at 60° C./1 mmHg for 7 hours to afford 310 mg. (88%) of 12a, melting at above 200° C. (slow dec.).

ir: $\nu_{max}^{KBr}$ 3400, 3150, 1760, 1700, 1680, 1600 cm$^{-1}$.
uv: $\lambda_{max}^{pH\ 7\ Buffer}$ 245 nm ($\epsilon$, 17100), 260 nm ($\epsilon$, 14100), 300 nm ($\epsilon$, 6500).

Anal. Calc'd for $C_{22}H_{21}N_7O_7S_3.3H_2O$: C, 40.90; H, 4.21; N, 15.17; S, 14.89. Found: H, 3.62; N, 15.87; S, 14.35.

Preparation of Monosodium Salt of BB-S483

To a suspension of 12a (280 mg., 0.47 m.mole) in 0.5 ml. of deionized water was added N NaOH to adjust to pH 9.5 and insoluble material was collected by filtration. Acetone (15 ml.) was added to the filtrate to separate the precipitate which was collected by filtration, washed with acetone (2×5 ml.) and dried at 70° C./1 mmHg for 7 hours to afford 220 mg. (76%) of monosodium salt of 12a. M.p. >210° C. (slow dec.). ir: $\nu_{max}^{KBr}$ 3400, 3250, 1760, 1710, 1650, 1600, 1550 cm$^{-1}$.
uv: $\epsilon_{max}^{pH\ 7\ Buffer}$ 245 nm ($\epsilon$, 19900), 260 nm ($\epsilon$, 16400), 300 nm ($\epsilon$, 6900).
nmr: $\delta_{ppm}^{D_2O}$ 3.60 (2H, m, 2—H), 3.91 (2H, s, CH$_2$CO), 4.12 (2H, s, C$\underline{H}_2$—NH$_2$), 4.20 (2H, m, 3—CH$_2$), 4.55 (2H, s, N—C$\underline{H}_2$CO), 4.95 (1H, d, J=4.5 Hz, 6—H), 5.50 (1H, d, J=4.5 Hz 7—H), 6.94 (1H, d, J=9 Hz, pyridazine—H), 6.99 (1H, d, J=4.5 Hz, thiophene—H$\beta$), 7.28 (1H, d, J=4.5 Hz, thiophene—H$\alpha$), 7.32 (1H, d, J=9 Hz, pyridazine—H).

Anal. Calc'd. for $C_{22}H_{20}N_7O_7S_3Na.1/2CH_3COCH_3$: C, 43.92; H, 3.61; N, 15.26; S, 14.97. Found: C, 43.48; H, 4.56; N, 15.28; S, 13.91.

Solubility

All of the monosodium salts in this series showed more than 10% solubility in water.

Nephrotoxicity

A preliminary nephrotoxicity study was carried out by administration of the test compound to a group of two rabbits at 100 mg./kg. intravenously. The results obtained with BB-S469 and BB-S479 indicated that they might have little nephrotoxic potential.

In vitro Activity (Table 1)

The MIC's were determined by the serial dilution method using Mueller-Hinton agar against 51 gram-positive and 96 gram-negative bacteria. The 147 test organisms were classified into 16 groups according to the genera and the types of antibiotic resistance, 5 groups for gram-positive and 11 for gram-negative bacteria. In Table 1 is shown the in vitro activity in terms of geometric mean of MIC's. BB-S472 and BB-S479 showed better overall activity than their non-N-methylated analogs, BB-S483 and BB-S469, respectively. BB-S479 was superior to BB-S472 in some species of gram-negative bacteria. Comparing with cefamandole, BB-S479 was more active against most of the test organisms except against Providencia species and Staphylococci.

TABLE 1

| | In vitro Activity Against 147 Test Organisms | | | | | | | |
|---|---|---|---|---|---|---|---|---|
| | | Geometric Mean MIC* (mcg./ml.) | | | | | | |
| Test Organism | No. of Strains | BB-S469 (Ex. 1) | BB-S472 (Ex. 2) | BB-S478 (Ex. 3) | BB-S479 (Ex. 4) | BB-S483 (Ex. 5) | Cefam-andole | BL-S786** |
| S. aureus (sensitive) | 4 | 0.4 | 0.4 | 0.4 | 0.3 | 0.3 | 0.1 | 1.3 |
| S. aureus penicil-linase+) | 13 | 1.2 | 0.9 | 1.0 | 0.9 | 1.1 | 0.4 | 3.0 |
| S. aureus (Methicillin-R) | 15 | 30 | 58 | 50 | 35 | 48 | 2.4 | 48 |
| S. pyogenes | 10 | 0.05 | 0.05 | 0.04 | 0.04 | 0.08 | 0.04 | 0.2 |
| D. pneumoniae | 9 | 0.03 | 0.05 | 0.03 | 0.04 | 0.04 | 0.2 | 0.08 |
| E. coli (sensitive) | 13 | 0.3 | 0.2 | 0.2 | 0.2 | 0.3 | 0.3 | 0.4 |
| E. coli (Penicillinase +) | 7 | 11 | 15 | 10 | 2.6 | 21 | 5.7 | 9.3 |
| Enterobacter (sensitive) | 3 | 1.0 | 1.3 | 0.8 | 0.5 | 1.3 | 1.0 | 1.3 |
| Enterobacter (Cephalosporinase +) | 7 | 4.7 | 3.2 | 2.6 | 2.1 | 5.2 | 4.7 | 7.7 |
| Proteus (indole−) | 6 | 0.6 | 0.3 | 0.4 | 0.5 | 0.7 | 0.6 | 0.9 |
| Proteus (indole +) | 14 | 0.5 | 0.3 | 0.3 | 0.2 | 0.4 | 0.5 | 0.7 |
| Proteus (indole +, cephalosporinase +) | 5 | 11 | 8.3 | 7.3 | 4.8 | 17 | 3.6 | 29 |
| Providencia sp. | 5 | 4.2 | 4.8 | 4.8 | 4.2 | 2.1 | 0.7 | 1.4 |
| Klebsiella sp. | 12 | 0.9 | 0.8 | 0.6 | 0.6 | 1.1 | 2.4 | 0.8 |
| S. marcescens | 16 | 130 | 200 | 40 | 35 | 81 | 34 | 180 |
| Miscellaneous (Salmonella, Shigella, Citrobacter) | 8 | 0.7 | 0.4 | 0.3 | 0.4 | 0.9 | 0.3 | 0.7 |

*Mueller-Hinton Agar (inoculum size: $10^{-4}$ dilution) MIC cut-off: 200 mcg./ml.
**BL-S786 is sodium 7-(2-aminomethylphenylacetamido)-3-(1-carboxymethyltetrazol-5-ylthiomethyl)-3-cephem-4-carboxylate

EXAMPLE 6

Substitution in the procedure of Example 3 for the 2-N-t-butoxycarbonyl-N-methylaminomethyl-4-hydroxyphenylacetic acid used therein of an equimolar weight of 2-N-t-butoxycarbonylaminomethyl-4-hydroxyphenylacetic acid and of 2-N-t-butoxycarbonylaminomethyl-4-methoxyphenylacetic acid and of 2-N-t-butoxycarbonyl-N-methylaminomethyl-4-methoxyphenylacetic acid, respectively, produces the compounds having the structures

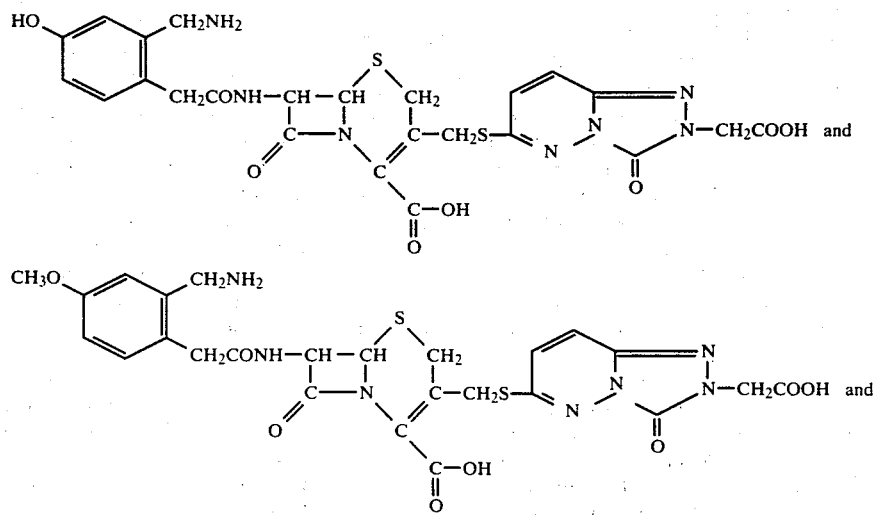

-continued

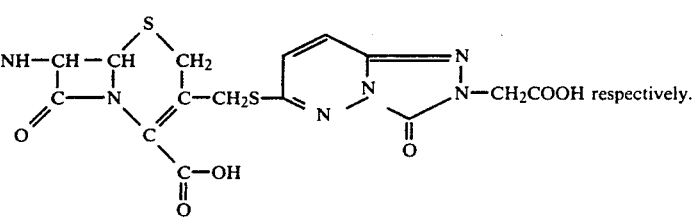
respectively.

EXAMPLE 7
Preparation of BB-S493

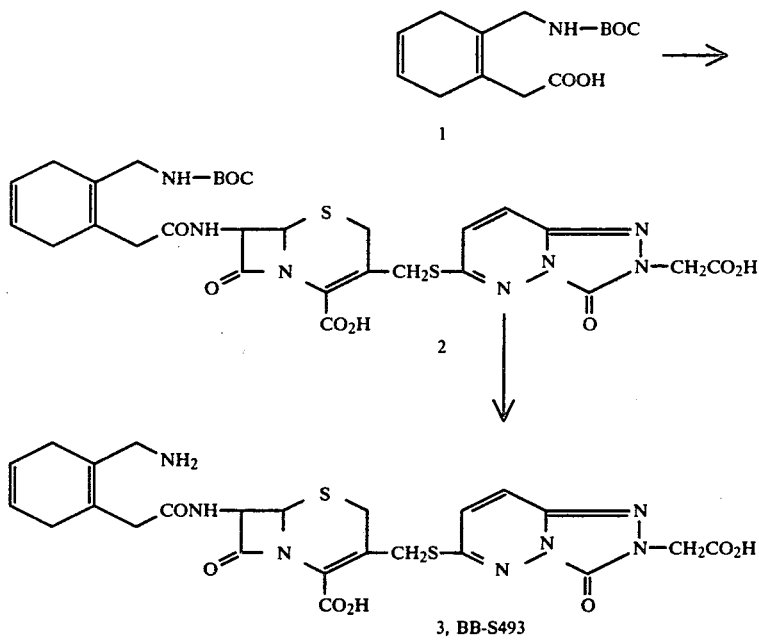

7-[(2-N-t-Butoxycarbonylaminomethyl-1,4-cyclohexadienyl)-acetamido]-3-(2-N-carboxymethyl-s-triazolo[4,5-b]pyridazin-3-on-6-ylthiomethyl)-3-cephem-4-carboxylic Acid (2)

A mixture of 2-N-t-butoxycarbonylaminomethyl-1,4-cyclohexadienylacetic acid (1, 640 mg., 2.4 m.mole), 2,4-dinitrophenol (422 mg., 2.4 m.mole) and DCC (494 mg., 2.4 m.mole) in 10 ml. of dry THF was stirred for 1.5 hours at room temperature. The precipitated urea was removed by filtration. The filtrate was added in one portion to a solution of 7-amino-3-(2-N-carboxymethyl-s-triazol[4,5-b]-pyridazin-3-on-6-ylthiomethyl)-3-cephem-4-carboxylic acid in 10 ml. of water containing triethylamine (0.56 ml., 4 m.mole) and the mixture was stirred at room temperature for 3 hours. The reaction mixture was concentrated to 10 ml. under reduced pressure, washed with ether (3×10 ml.), acidified with 6 N hydrochloric acid and extracted with ethyl acetate (5×10 ml.). The combined extracts were washed with a saturated saline solution and dried with anhydrous $Na_2SO_4$. The solvent was evaporated and the residue was chromatographed on silica gel (Wako-gel C-200, 30 g.) eluting with chloroform-methanol (0–50%). The fractions containing the desired product were collected. The solvent was removed and the residue was triturated with ether-n-hexane to give 410 mg. (30%) of the product 2. M.p. 110° C. (decomp.).

ir: $\nu_{max}^{KBr}$ 1780, 1730, 1610, 1530, 1250, 1160 cm$^{-1}$.

uv: $\lambda_{max}^{Buff(pH\,7)}$ 252 nm ($\epsilon$, 19000), 300 nm ($\epsilon$, 8600, sh).

Anal. Calc'd. for $C_{29}H_{33}N_7O_9S_2.2H_2O$: C, 48.12; H, 5.15; N, 13.54; S, 8.86. Found: C, 48.07; H, 4.64; N, 12.70; S, 8.39.

BB-S493;
7-[(2-Aminomethyl-1,4-cyclohexadienyl)acetamido]3-(2-N-carboxymethyl-s-triazolo[4,5-b]pyridazin-3-on-6-ylthiomethyl)-3-cephem-4-carboxylic Acid (3)

The N-BOC-protected cephalosporin 2 (350 mg., 0.51 m.mole) was treated with trifluoroacetic acid (TFA) (1 ml.) for 30 minutes at room temperature. To the mixture was added ether (50 ml.) to give the TFA salt of 3, which was collected by filtration and then dissolved in a mixture of acetonitrile (5 ml.) and water (2 ml.). The solution was treated with a small amount of active carbon, adjusted to pH 6 with concentrated ammonium hydroxide. The precipitate was collected, washed with acetonitrile (5 ml.) and dried in vacuo to afford 235 mg. (78%) of 3. M.p. 220°–230° C. (decomp.).

ir: $\nu_{max}^{KBr}$ 1770, 1740, 1710, 1650, 1600, 1550 cm$^{-1}$.
uv: $\lambda_{max}^{Buff(pH\,7)}$ 252 nm ($\epsilon$, 20000), 300 nm ($\epsilon$, 9000, sh).

Anal. Calc'd. for $C_{24}H_{25}N_7O_7S_2.H_2O$: C, 47.60; H, 4.49; N, 16.19; S, 10.59. Found: C, 47.77; H, 4.06; N, 16.49; S, 10.64.

| In vitro Antibacterial Activity of BB-S493 Compared with BB-S479 and Cefamandole (Determined by Steers' Agar Dilution Method on Mueller-Hinton Agar Plate) | | | | |
|---|---|---|---|---|
| | | MIC (mcg./ml.) | | |
| Organism | | BB-S493 | BB-S479 | Cefamandole |
| S. aureus Smith | A9537 | 0.4 | 0.4 | 0.1 |
| S. aureus | A9497 | 0.2 | 0.1 | 0.05 |
| S. aureus BX-1633 | A9606 | 0.4 | 0.4 | 0.2 |
| St. faecalis | A9536 | 100 | 100 | 50 |
| E. coli NIHJ | | 0.1 | 0.05 | 0.025 |
| E. coli ATCC 8739 | | 0.2 | 0.05 | 0.05 |
| E. coli Juhl | A15119 | 0.2 | 0.1 | 0.4 |
| E. coli BX-1373 | | 0.4 | 0.2 | 0.4 |
| E. coli | A15810 | 0.2 | 0.1 | 0.2 |
| E. coli | A9660 | 0.1 | 0.05 | 0.1 |
| E. coli | A15147 | 6.3 | 3.1 | 3.1 |
| Kl. pneumoniae | A9678 | 0.4 | 0.4 | 1.6 |
| Kl. pneumoniae | A9977 | 0.2 | 0.1 | 0.4 |
| Kl. pneumoniae | A15130 | 0.2 | 0.1 | 0.4 |
| Kl. pneumoniae | A9867 | 0.2 | 0.1 | 0.8 |
| Pr. vulgaris | A9436 | 0.4 | 0.1 | 0.2 |
| Pr. vulgaris | A9699 | 6.3 | 0.8 | 25 |
| Pr. mirabilis | A9554 | 0.2 | 0.1 | 0.8 |
| Pr. mirabilis | A9900 | 0.2 | 0.1 | 0.8 |
| Pr. morganii | A9553 | >100 | >100 | >100 |
| Pr. morganii | A20031 | 0.4 | 0.1 | 0.8 |
| Pr. rettgeri | A15167 | 0.1 | 0.1 | 0.1 |
| Ps. aerugionsa | A9930 | >100 | >100 | >100 |
| Ps. aeruginosa | A9843 | >100 | >100 | >100 |
| Shig dysenteriae | | 0.05 | 0.025 | 0.2 |
| Shig. flexneri | A9684 | 25 | 12.5 | 3.1 |
| Shig. sonnei | A9516 | 0.05 | 0.025 | 0.05 |
| Serr. marcescens | A20019 | 100 | 25 | 50 |
| Enterob. cloacae | A9656 | 6.3 | 1.6 | 3.1 |
| Sal. enteritidis | A9531 | 0.1 | 0.05 | 0.1 |
| Sal. typhosa | A9498 | 0.1 | 0.05 | 0.1 |
| B. anthracis | A9504 | 0.0125 | 0.025 | 0.2 |

| In vivo Activity of BB-S479 and Related Compounds (Mice, sc) | | | | | | | | |
|---|---|---|---|---|---|---|---|---|
| | (PD$_{50}$ (mgm./kg.) | | | | | | | |
| Organism | BB-S469 | BB-S472 | BB-S478 | BB-S479 | BB-S483 | BB-S493 | Cefamandole | BL-S786 |
| S. aureus Smith | 0.19 | 0.12 | 0.08 | 0.16 | 0.34 | 0.29 | 0.93 | 0.53 |
| | 0.16 | | | 0.12 | | | 0.74 | 0.55 |
| | 0.29 | | | 0.2 | | | 0.6 | 0.94 |
| | 0.2 | | | | | | 0.8 | 0.46 |
| | | | | | | | 0.8 | 0.6 |
| E. coli Juhl | 0.19 | 0.19 | 0.08 | 0.19 | 0.15 | 0.27 | 0.95 | 0.43 |
| | 0.24 | | | 0.15 | | | 1.7 | 0.55 |
| | 0.15 | | | 0.12 | | | 1.8 | 0.46 |
| | | | | | | | 2.2 | 0.39 |
| | | | | | | | 0.8 | |

Additional Starting Materials

6-Chloro-2-(2-cyanoethyl)-2,3-dihydro-s-triazolo[4,3-b]pyridazin-3-on

To a solution of 6-chloro-2,3-dihydro-s-triazolo[4,3-b]pyridazin-3-on [P. Francabilla and F. Lauria, J. Het. Chem. 8, 415 (1971)] (17 g., 0.1 mole) in dry DMF (300 ml.) was added potassium tert.-butoxide (0.5 g., 4.5 m.moles) with stirring. Acrylonitrile (6.6 g., 0.2 mole) in dry DMF (10 ml.) was added to the mixture. The mixture was stirred at 100°–110° C. for 24 hours, then poured into water (700 ml.) and extracted with ethyl acetate (5×400 ml.). The organic extracts were combined, dried over Na$_2$SO$_4$ and evaporated. The residue was crystallized from ethyl acetate to give light yellow needles of 6-chloro-2-(2-cyanoethyl)-2,3-dihydro-s-triazolo[4,3-b]pyridazin-3-on (2.5 g., 11%). M.p. 166°–168° C.

ir: $\nu_{max}^{KBr}$ 2230, 1720, 1550, 1500 cm$^{-1}$.

uv: $\lambda_{max}^{dioxane}$ 373 nm ($\epsilon$2000).

nmr: $\delta_{ppm}^{DMSO-d6}$ 3.03 (2H, t, J=6.0 Hz, CH$_2$), 4.21 (2H, t, J=6.0 Hz, CH$_2$), 7.23 (1H, d, J=10.0 Hz, pyridazine—H), 7.93 (1H, d, J=10.0 Hz, pyridazine—H).

Anal. Calc'd. for C$_8$H$_6$N$_5$OCl: C, 42.97; H, 2.70; N, 31.32; Cl, 15.86. Found: C, 42.73, 42.56; H, 2.57, 2.50; N, 31.36, 31.68; Cl, 15.96, 15.81.

2-(2-Carboxyethyl)-6-chloro-2,3-dihydro-s-triazolo[4,3-b]pyridazin-3-on

A solution of 6-chloro-2-(2-cyanoethyl)-2,3-dihydro-s-triazolo[4,3-b]pyridazin-3on (724 mg.) in 6N-HCl (15 ml.) was refluxed for 6 hours. The reaction mixture was extracted with ethyl acetate (10×20 ml.). The combined extracts were washed with saturated aqueous sodium chloride (50 ml.), dried over Na$_2$SO$_4$ and evaporated to give light yellow, solid 2-(2-carboxyethyl)-6-chloro-2,3-dihydro-s-triazolo[4,3-b]pyridazin-3-on (567 mg., 72%). M.p.>170° C. (sublimation).

ir: $\nu_{max}^{KBr}$ 3400–2400, 1730, 1710, 1540 cm$^{-1}$.

uv: $\lambda_{max}^{dioxane}$ 377 nm ($\epsilon$1500).

nmr: $\delta_{ppm}^{D2O+NaHCO3}$ 2.70 (2H, t, J=7.0 Hz, CH$_2$), 4.24 (2H, t, J=7.0 Hz, CH$_2$), 7.17 (1H, d, J=10.0 Hz, pyridazine—H), 7.70 (1H, d, J=10.0 Hz, pyridazine—H).

Anal. Calc'd. for C$_8$H$_7$N$_4$O$_3$Cl: C, 39.60; H, 2.91; N, 23.09; Cl, 14.61. Found: C, 39.62, 39.48; H, 2.97, 2.67; N, 23.05, 22.70; Cl. 13.93, 14.12.

2-(2-Carboxyethyl)-2,3-dihydro-6-mercapto-s-triazolo[4,3b]pyridazin-3-on

A mixture of 2-(2-carboxyethyl)-6-chloro-2,3-dihydro-s-triazolo[4,3-b]pyridazin-3-on (567 mg., 2.34 m.moles) and 70% sodium hydrosulfide dihydrate (924 mg., 7.02 m.mole) in water (10 ml.) was stirred at room temperature for two hours. The reaction mixture was adjusted successively to pH 1 with c. HCl, to pH 10 with NaOH and then to pH 1 with c. HCl. The resulting precipitate of 2-(carboxyethyl)-2,3-dihydro-6-mercapto-s-triazolo[4,3-b]pyridazin-3-on was collected by filtration and washed with water. Yield: 418 mg. (74%). M.p. 174°–176° C.

ir: $\nu_{max}^{KBr}$ 3600–2600, 2440, 1730, 1720 (sh) cm$^{-1}$.

uv: $\epsilon_{max}^{pH\ 7\ buffer}$ 262 nm ($\epsilon$17000), 318 nm ($\epsilon$6600).

nmr: $\delta_{ppm}^{DMSO-d6}$ 2.73 (2H, t, J=7.0 Hz, CH$_2$), 4.07 (2H, t, J=7.0 Hz, CH$_2$), 7.30 (1H, d, J=10.0 Hz. pyridazine-H), 7.74 (1H, d, J=10.0 Hz, pyridazine—H).

Anal. Calc'd. for C$_8$H$_8$N$_4$O$_3$S: C, 40.00; H, 3.36; N, 23.32; S, 13.35. Found: C, 39.08, 39.06; H, 3.12, 3.20; N, 22.65, 22.70; S, 14.23, 14.29.

7-Amino-3-[2-(2-carboxyethyl)-2,3-dihydro-s-triazolo[4,3-b]pyridazin-3-on-6-ylthiomethyl]-3-cephem-4-carboxylic Acid.

A mixture of 7-ACA (405 mg., 1.49 m.moles), the thiol 2-(2-carboxyethyl)-2,3-dihydro-6-mercapto-s-triazolo[4,3-b]pyridazin-3-on (357 mg., 1.49 m.moles) and NaHCO$_3$ (375 mg., 4.47 m.moles) in 0.1 M phosphate buffer (pH 7, 8 ml.) was stirred at 80° C. for 30 minutes. The reaction mixture was cooled and filtered to remove insolubles. The filtrate was adjusted to pH 1–2 with c. HCl. The resulting precipitate, 7-amino-3-[2-(2-carboxyethyl)-2,3-dihydro-s-triazolo[4,3-b]pyridazin-3-on-6-ylthiomethyl]-3-cephem-4-carboxylic acid, was collected by filtration and washed with water. Yield: 519 mg. (77%).

ir: $\nu_{max}^{KBr}$ 3600–2200, 1800, 1725, 1620, 1550, 1480 cm$^{-1}$.

uv: $\lambda_{max}^{pH\ 7\ buffer}$ 253 nm ($\epsilon$20000), 298 nm ($\epsilon$10000).

nmr: $\delta_{ppm}^{D2O+K2CO3}$ 2.20 (2H, t, J=7.0 Hz, CH$_2$), 3.40 (1H, d, J=17.5 Hz, 2—H), 3.85 (1H, d, J=17.5 Hz, 2—H), 4.00–4.50 (4H, m, 3-CH$_2$ and N-CH$_2$-), 5.01 (1H, d, J=4.0 Hz, 6-H), 5.40 (1H, d, J=4.0 Hz, 7-H), 6.94 (1H, d, J=10.0 Hz, pyridazine-H), 7.44 (1H, d, J=10.0 Hz, pyridazine—H).

Anal. Calc'd. for C$_{16}$H$_{16}$N$_6$O$_6$S$_2$.3/2H$_2$O: C, 40.09; H, 3.99; N, 17.52; S, 13.37. Found: C, 40.06, 40.12; H, 3.33, 3.34; N, 16.96, 16.98; S, 13.87, 13.98.

7-ACA refers to 7-aminocephalosporanic acid and DMF to dimethylformamide.

EXAMPLE 8

7-[o-(N-Butoxycarbonyl-N-methylaminomethyl)-phenylacetamido]-3-[2-(2-carboxyethyl)-2,3-dihydro-s-triazolo[4,3-b]pyridazin-3-on-6-ylthiomethyl]-3-cephem-4-carboxylic acid To a mixture of 7-amino-3-[2-(2-carboxyethyl)-2,3-dihydro-s-triazolo[4,3-b]pyridazin-3-on-6-ylthiomethyl]-3-cephem-4-carboxylic acid (452 mg., 1 m.mole) and triethylamine (0.46 ml., 3.3 m.mole) in 50% aqueous acetonitrile (4 ml.) was added a THF solution (3 ml.) of 2,4-dinitrophenyl o-(N-t-butoxycarbonyl-N-methylaminomethyl)phenylacetate prepared from o-(N-t-butoxycarbonyl-N-methylaminomethyl)phenylacetic acid (283 mg., 1.1 m.mole), 2,4-dinitrophenol (202 mg., 1.1 m.mole) and DCC (227 mg., 1.1 m.mole). The mixture was stirred at room temperature overnight and concentrated under reduced pressure to remove the organic solvents. The aqueous concentrate was washed with ether (3×20 ml.), acidified with c.HCl to pH 1–2 and extracted with ethyl acetate (5×20 ml.). The combined extracts were dried with anhydrous Na$_2$SO$_4$ and evaporated to dryness. The residue was chromatographed on a column of silica gel (Wako gel, C-200, 10 g.) by eluting with a mixture of MeOH-CHCl$_3$ (MeOH: 0 to 3%). The combined eluates which contained the desired product were evaporated to give 359 mg. (50%) of the title compound. M.p.>150° C. (dec.).

ir: $\nu_{max}^{KBr}$ 3600–2400, 1780, 1720, 1680, 1550, 1490 cm$^{-1}$.

uv: $\lambda_{max}^{pH\ 7\ Buffer}$ 253 nm ($\epsilon$19800), 298 nm ($\epsilon$9400).

nmr: $\delta_{ppm}^{DMSO-d6}$ 1.37 (9H, s, t-Bu-H), 2.70 (3H, s, N-CH$_3$), 2.70 (2H, t, J=7.0 Hz, —CH$_2$—), 3.2–4.5 (10H, m), 5.01 (1H, d, J=5 Hz, 6-H), 5.60 (1H, d-d, J=5 & 8 Hz, the 8 Hz coupling disappeared by addition of D$_2$O, 7—H), 6.93 (1H, d, J=10 Hz, pyridazine—H). 7.58 (1H, d, J=10 Hz, pyridazine—H).

Anal. Calcd. for C$_{31}$H$_{35}$N$_7$O$_9$S$_2$.5/2H$_2$O: C, 49.08; H, 5.31; N, 12.92; S, 8.45. Found: C, 49.32; 49.36; H, 4.70, 4,63; N, 12.52; 12.53; S, 8.44, 8.43.

BB-S 525;
7-[o-(N-Methylaminomethyl)phenylacetamido]-3-[2-(2-carboxyethyl)-2,3-dihydro-s-triazolo[4,3-b]pyridazin-3-on-6-ylthiomethyl]-3-cephem-4-carboxylic acid A mixture of trifluoroacetic acid (1 ml.) and the BOC-protected cephalosporin prepared above (302 mg., 0.42 m.mole) was allowed to stand at room temperature for 15 min. and then diluted with ether (10 ml.). The resulting precipitate was collected by filtration and washed with dry ether (2×10 ml.) to afford 263 mg. of solid which was dissolved in a mixture of water (6 ml.) and acetonitrile (3 ml.). The stirred solution was adjusted at pH 4 with 1 N-NaOH (0.36 ml.) and diluted with acetonitrile (100 ml.) to give the precipitate (187 mg.), which was suspended in water (4 ml.) and adjusted at pH 9 with sodium hydroxide (1 N, 0.3 ml.). The solution was treated with a small amount of active carbon and freeze-dried to leave the monosodium salt of BB-S 525. Yield 106 mg. (39%). M.p.>180° C. (dec.).

ir: $\nu_{max}^{KBr}$ 3600–2400, 1770, 1710, 1600, 1490, 1400 cm$^{-1}$.

uv: $\lambda_{max}^{pH\ 7\ Buffer}$ 253 nm ($\epsilon$19800), 298 nm ($\epsilon$8800).

nmr: $\delta_{max}^{D2O}$ 2.70 (2H, m, —CH$_2$—), 2.75 (3H, s, N-CH$_3$), 4.4–3.4 (10H, m), 4.92 (1H, d, J=4.0 Hz, 6-H), 5.55 (1H, d, J=4.0 Hz, 7—H), 6.93 (1H, d, J=9.5 Hz, pyridazine—H), 7.28 (4H, s, Ph—H), 7.40 (1H, d, J=9.5 Hz, pyridazine—H).

Anal. Calcd. for C$_{26}$H$_{26}$N$_7$O$_7$S$_2$.Na.3H$_2$O: C, 45.28; H, 4.68; N, 14.22; S, 9.30. Found: C, 45.34, 44.84; H, 4.01, 3.85; N, 14.14, 14.08; S, 9.76.

| In vitro antibacterial activity of BB-S 525 compared with BB-S 479 and cefamandole (determined by Steers' agar dilution method on Mueller-Hinton agar plate) | | | |
|---|---|---|---|
| | MIC (mcg./ml) | | |
| Organism | BB-S 525 | BB-S 479 | Cefamandole |
| S. aureus Smith | 0.4 | 0.4 | 0.2 |
| S. aureus | 0.2 | 0.2 | 0.05 |
| S. aureus BX-1633 | 0.8 | 0.8 | 0.2 |
| St. faecalis | >100 | >100 | 100 |
| E. coli NIHJ | 0.2 | 0.1 | 0.1 |
| E. coli ATCC 8739 | 6.3 | 3.1 | 6.3 |
| E. coli Juhl | 0.4 | 0.2 | 0.4 |
| E. coli BX-1373 | 0.4 | 0.2 | 0.2 |
| E. coli | 0.2 | 0.1 | 0.1 |
| E. coli | 0.2 | 0.05 | 0.05 |
| E. coli | 6.3 | 3.1 | 1.6 |
| Kl. pneumoniae | 1.6 | 0.8 | 3.1 |
| Kl. pneumoniae | 0.2 | 0.1 | 0.2 |
| Kl. pneumoniae | 0.2 | 0.2 | 0.8 |
| Kl. pnuemoniae | 0.2 | 0.2 | 0.8 |
| Pr. vulgaris | 0.2 | 0.2 | 0.2 |
| Pr. vulgaris | 3.1 | 0.8 | 50 |
| Pr. mirabilis | 0.4 | 0.1 | 0.4 |
| Pr. mirabilis | 0.2 | 0.1 | 0.2 |
| Pr. morganii | >100 | >100 | 3.1 |
| Pr. morganii | 0.2 | 0.2 | 0.8 |
| Pr. rettgeri | 0.8 | 0.8 | 0.1 |
| Ps. aeruginosa | >100 | >100 | >100 |
| Ps. aeruginosa | >100 | >100 | >100 |
| Shig. dysenteriae | 0.1 | 0.1 | 0.1 |
| Shig. flexneri | 12.5 | 12.5 | 3.1 |
| Shig. sonnei | 0.1 | 0.1 | 0.2 |
| Serr. marcescens | 25 | 12.5 | 50 |
| Enterob. cloacae | 3.1 | 3.1 | 1.6 |
| Sal. enteritidis | 0.2 | 0.1 | 0.1 |
| Sal. typhosa | 0.2 | 0.1 | 0.1 |
| B. anthracis | 0.2 | 0.2 | 0.05 |

EXAMPLE 9

Substitution in the procedure of Example 8 for the 2-N-t-butoxycarbonyl-N-methylaminomethyl-4-hydroxyphenylacetic acid used therein of an equimolar weight of 2-N-t-butoxycarbonylaminomethyl-4-hydroxyphenylacetic acid and of 2-N-t-butoxycarbonylaminomethyl-4-methoxyphenylacetic acid and of 2-N-t-butoxycarbonyl-N-methylaminomethyl-4-methoxyphenylacetic acid, respectively, produces the compounds having the stuctures

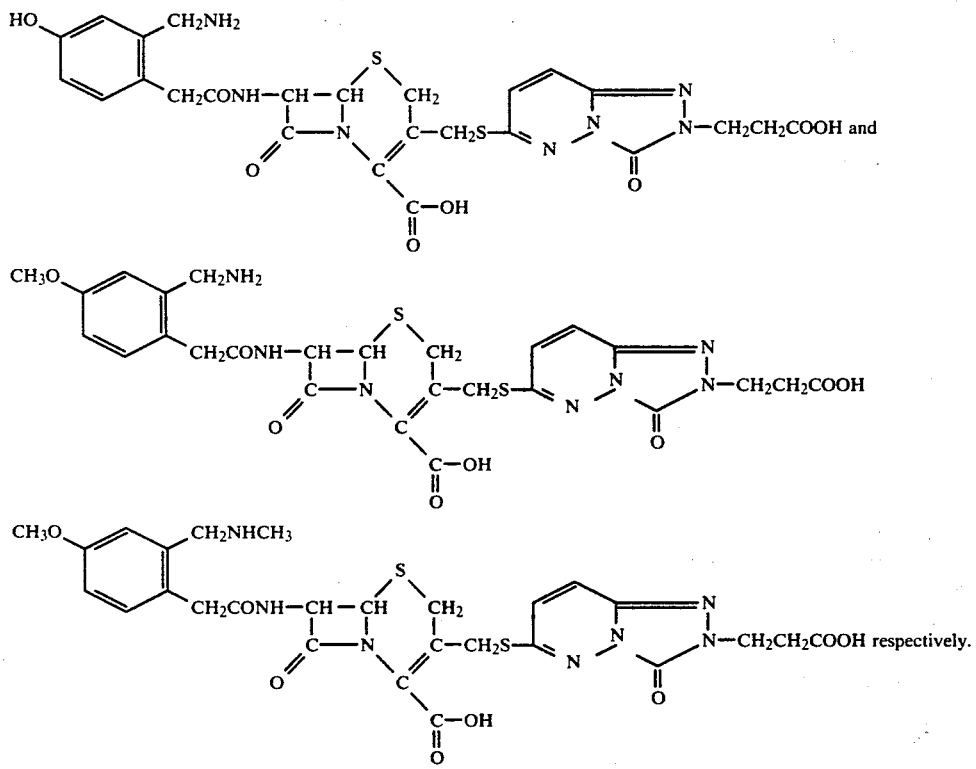

There is also provided by the present invention a compound having the formula

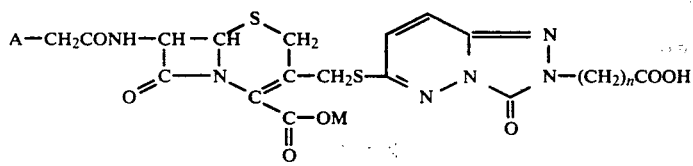

wherein A represents

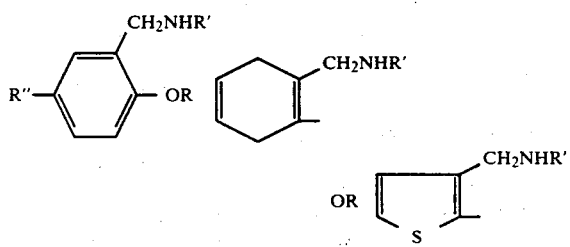

wherein R" is hydrogen, hydroxy or methoxy; R' is hydrogen or methyl; n is one or two and M is

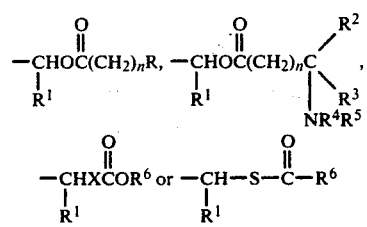

$n$ is 0 to 4; R is hydrogen, alkyl having 1 to 8 carbon atoms, cycloalkyl of 3 to 6 carbon atoms, phenyl, $C_1$-$C_4$ phenalkyl, pyridyl, thienyl, or pyrrolyl; $R^1$ is hydrogen, methyl or ethyl; $R^2$ and $R^3$ are each hydrogen, alkyl having 1 to 6 carbon atoms, phenyl, pyridyl, or thienyl; $R^4$ and $R^5$ are each hydrogen or alkyl of 1 to 4 carbon atoms; $R^6$ is alkyl having 1 to 4 carbon atoms, phenyl, phenalkyl having 1 to 4 carbon atoms, pyridyl, thiadiazolyl, amino or $C_1$-$C_4$ alkylamino; X is NH or oxygen; and each phenyl group is unsubstituted or substituted with one or two substituents selected from the group consisting of alkyl having 1 to 6 carbon atoms, alkoxy having 1 to 4 carbon atoms, hydroxy, amino, $NHR^1$, $N(R^1)_2$, nitro, fluoro, chloro, bromo or carboxy, or a nontoxic, pharmaceutically acceptable salt thereof.

There is also provided by the present invention a compound having the formula

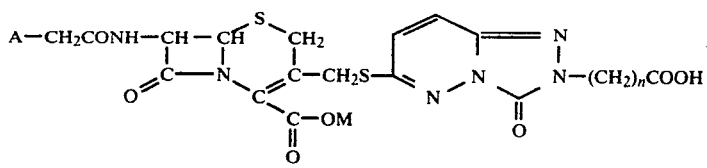

wherein A represents

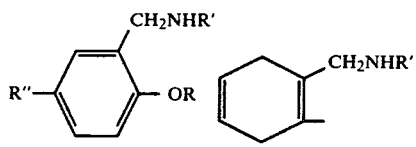

wherein R″ is hydrogen, hydroxy or methoxy; $R^1$ is hydrogen or methyl; n is one or two and M is selected from the group consisting of

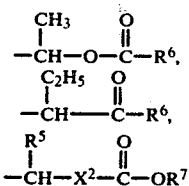

wherein $R^5$ is a hydrogen atom, a methyl or an ethyl group; $X^2$ is —O—, —NH—; $R^6$ is a basic group such as alkyl or aralkyl substituted with substituted or unsubstituted $NH_2$, such as alkyl-$NHCH_3$, aralkyl-$NHCH_3$,

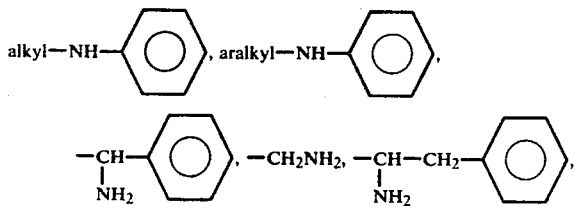

$R^7$ is an alkyl group such as a methyl, ethyl, propyl, isopropyl, butyl, isobutyl, pentyl or 2-ethyl-hexyl group; a cycloalkyl group such as cyclopropyl, cyclobutyl, cyclopentyl, cyclohexyl or cycloheptyl; an aryl group such as phenyl or naphthyl; an aralkyl group such as benzyl or naphthylmethyl; a heterocyclic group and wherein the alkyl, cycloalkyl, aryl, aralkyl and heterocyclic groups may be substituted with one or more groups selected from the class consisting of amino groups, substituted amino groups such as methylamino, diethylamino or acetamido groups, the halogen groups such as fluorine, chlorine or bromine, nitro groups, alkoxy groups such as methoxy, ethoxy, propyloxy, isopropyloxy, butoxy or isobutoxy; or a nontoxic, pharmaceutically acceptable salt thereof.

There is also provided by the present invention a compound having the formula

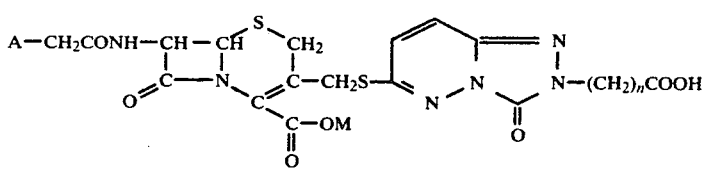

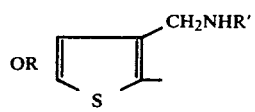

wherein A represents

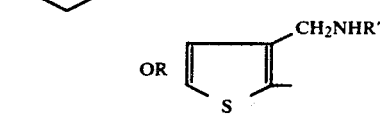

wherein R″ is hydrogen, hydroxy or methoxy; R′ is hydrogen or methyl; n is one or two and M is

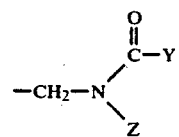

wherein Y is alkyl of one to six carbon atoms, phenyl, benzyl, alkoxy of one to six carbon atoms, or benzyloxy; Z is alkyl of one to six carbon atoms, phenylbenzyl, alkoxy of one to six carbon atoms, cyclopentyl, cyclohexyl and phenyl, or Y+Z taken together are a 3-benzoxazolidine ring; or a nontoxic, pharmaceutically acceptable salt thereof.

Also included within the present invention are pharmaceutical compositions comprising a mixture of an antibacterially effective amount of a compound of the present invention and a semisynthetic penicillin or another cephalosporin or a cephamycin or a β-lactamase inhibitor or an aminoglycoside antibiotic.

There is further provided by the present invention a pharmaceutical composition comprising an antibacterially effective amount of a compound having the formula

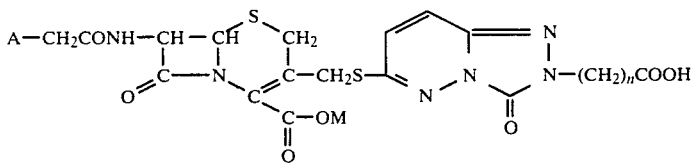

wherein A represents

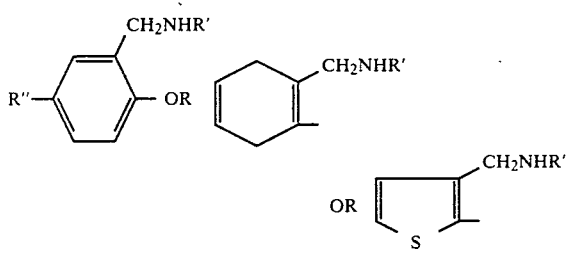

wherein R″ is hydrogen, hydroxy or methoxy; R′ is hydrogen or methyl; n is one or two and M is hydrogen, pivaloyloxymethyl, acetoxymethyl, methoxymethyl, acetonyl, phenacyl, p-nitrobenzyl, $\beta\beta\beta$-trichloroethyl, 3-phthalidyl or 5-indanyl or a nontoxic, pharmaceutically acceptable salt thereof.

There is also provided by the present invention a method for combatting Shig. dysenteriae infections which comprises administering to a warm-blooded mammal infected with a Shig. dysenteriae infection an amount effective for treating said Shig. dysenteriae infection of a composition comprising a compound having the formula

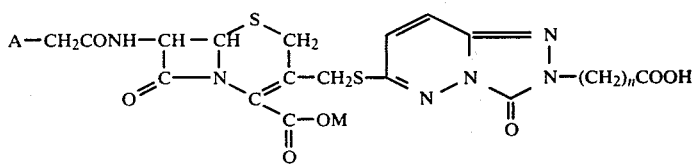

hydrogen or methyl; n is one or two and M is hydrogen, pivaloyloxymethyl, acetoxymethyl, melthoxymethyl, acetonyl, phenacyl, p-nitrobenzyl, $\beta\beta\beta$-trichloroethyl, 3-phthalidyl or 5-indanyl and preferably is hydrogen or a nontoxic, pharmaceutically acceptable salt thereof.

There is further provided by the present invention a method of treating bacterial infections comprising administering by injection to an infected warm-blooded animal, including man, an effective but nontoxic dose of 250–1000 mgm. of a compound having the formula wherein A represents

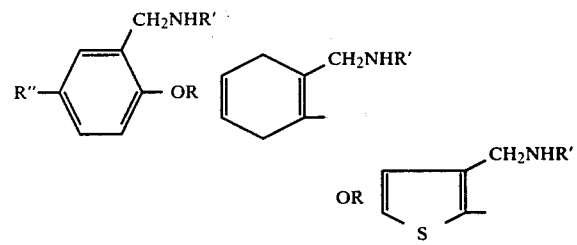

wherein R″ is hydrogen, hydroxy or methoxy; R′ is hydrogen or methyl; n is one or two and M is hydrogen, pivaloyloxymethyl, acetoxymethyl, methoxymethyl, acetonyl, phenacyl, p-nitrobenzyl, $\beta\beta\beta$-trichloroethyl, 3-phthalidyl or 5-indanyl and preferably is hydrogen or a nontoxic, pharmaceutically acceptable salt thereof.

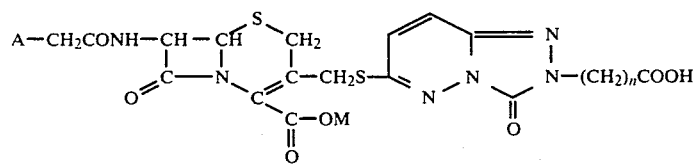

wherein A represents

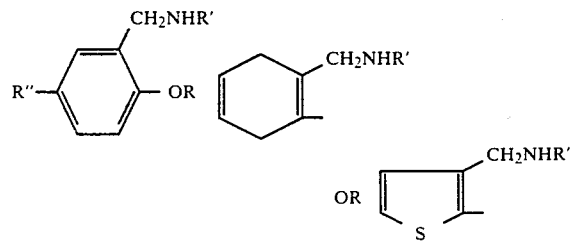

There is also provided by the present invention a method for combatting B. anthracis infections which comprises administering to a warm-blooded mammal infected with a B. anthracis infection an amount effective for treating said B. anthracis infection of a conposition comprising a compound having the formula

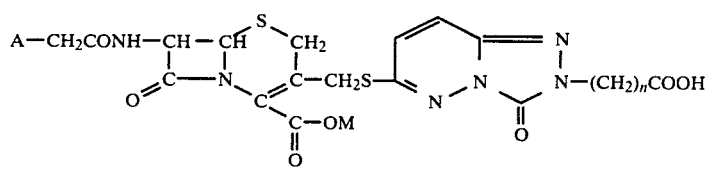

wherein A represents

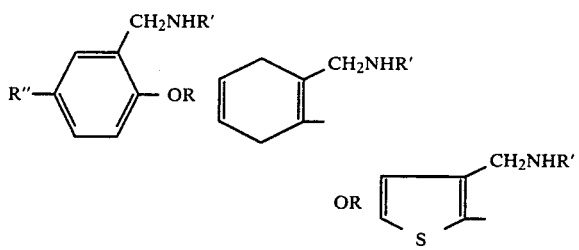

wherein R" is hydrogen, hydroxy or methoxy; R' is hydrogen or methyl; n is one or two and M is hydrogen, pivaloyloxymethyl, acetoxymethyl, methoxymethyl, acetonyl, phenacyl, p-nitrobenzyl, βββ-trichloroethyl, 3-phthalidyl or 5-indanyl and preferably is hydrogen or a nontoxic, pharmaceutically acceptable salt thereof.

We claim:

1. A compound having the formula

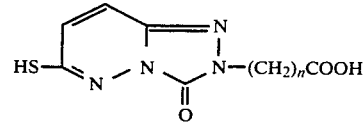

wherein n is one or two.

2. The compound of claim 1 wherein n is one.
3. The compound of claim 1 wherein n is two.

* * * * *